(12) United States Patent
Cheema et al.

(10) Patent No.: US 12,201,517 B2
(45) Date of Patent: Jan. 21, 2025

(54) TRANSCATHETER HEART VALVE APPARATUS FOR CALCIFIC MITRAL STENOSIS

(71) Applicant: Cardiovascular Diagnostics Inc., Mississauga (CA)

(72) Inventors: Asim Cheema, Mississauga (CA); Farrokh Janabi-Sharifi, North York (CA); Seyed Mohammad Rajaai, Toronto (CA)

(73) Assignee: Cardiovascular Diagnostics Inc., Mississauga (CA)

( * ) Notice: Subject to any disclaimer, the term of this patent is extended or adjusted under 35 U.S.C. 154(b) by 0 days.

(21) Appl. No.: 16/486,625

(22) PCT Filed: Feb. 16, 2018

(86) PCT No.: PCT/CA2018/050178
§ 371 (c)(1),
(2) Date: Aug. 16, 2019

(87) PCT Pub. No.: WO2018/148839
PCT Pub. Date: Aug. 23, 2018

(65) Prior Publication Data
US 2020/0008936 A1    Jan. 9, 2020

Related U.S. Application Data

(60) Provisional application No. 62/460,285, filed on Feb. 17, 2017.

(51) Int. Cl.
*A61F 2/24*    (2006.01)
(52) U.S. Cl.
CPC .......... *A61F 2/2418* (2013.01); *A61F 2/2433* (2013.01); *A61F 2/2412* (2013.01);
(Continued)

(58) Field of Classification Search
CPC .................. A61F 2/2418; A61F 2/2433; A61F 2210/0014; A61F 2220/0016;
(Continued)

(56) References Cited

U.S. PATENT DOCUMENTS 5,370,683 A  * 12/1994  Fontaine ................... A61F 2/90
                                                       606/198
6,214,054 B1    4/2001  Cunanan et al.
(Continued)

FOREIGN PATENT DOCUMENTS

CA         2874208 A1    11/2013
WO      2009132187 A1    10/2009

OTHER PUBLICATIONS

Webb et al., "Percutaneous transvenous mitral annuloplasty," Circulation, vol. 113, No. 6, pp. 851-855, 2006.
(Continued)

*Primary Examiner* — Leslie A Lopez
(74) *Attorney, Agent, or Firm* — SMART & BIGGAR LP; Tonino Rosario Orsi

(57) ABSTRACT

Examples of a mitral heart valve apparatus are described. In one example, the apparatus has an annular body made of a first material, and a plurality of first anchor members and at least two paddles made of a second material extending from the annular body. In a compressed state, the first anchor members extend substantially longitudinally from the first end of the annular body, and the paddles extend substantially longitudinally from the second end of the annular body. In an expanded state, the annular body has a larger diameter, the first anchor members extend outward from the first end for engaging an upstream portion of a mitral valve annulus to resist displacement of the annular body towards a left ventricle, and the paddles extend outward from the second end for engaging chordae tendineae. In another example, the
(Continued)

annular body, anchor members, and paddles are made of the same material.

27 Claims, 20 Drawing Sheets

(52) U.S. Cl.
CPC .............. *A61F 2210/0014* (2013.01); *A61F 2220/0016* (2013.01); *A61F 2220/0058* (2013.01); *A61F 2230/0021* (2013.01); *A61F 2250/0035* (2013.01); *A61F 2250/0037* (2013.01); *A61F 2250/0039* (2013.01); *A61F 2310/00023* (2013.01); *A61F 2310/00029* (2013.01)

(58) Field of Classification Search
CPC ...... A61F 2230/0021; A61F 2230/0013; A61F 2250/0069; A61F 2250/0039; A61F 2250/0036; A61F 2250/0018; A61F 2/2409; A61F 2220/0025; A61F 2250/0037; A61F 2002/30004; A61F 2002/4435
See application file for complete search history.

(56) References Cited

U.S. PATENT DOCUMENTS

| | | |
|---|---|---|
| 6,269,819 B1 | 8/2001 | Oz et al. |
| 6,461,366 B1 | 10/2002 | Seguin |
| 6,547,827 B2 | 4/2003 | Carpentier et al. |
| 6,629,534 B1 | 10/2003 | Goar et al. |
| 6,752,813 B2 | 6/2004 | Goldfarb et al. |
| 6,770,083 B2 | 8/2004 | Seguin |
| 6,793,673 B2 | 9/2004 | Kowalsky et al. |
| 6,824,562 B2 | 11/2004 | Mathis et al. |
| 6,908,481 B2 | 6/2005 | Cribier |
| 6,960,229 B2 | 11/2005 | Mathis et al. |
| 6,964,683 B2 | 11/2005 | Kowalsky et al. |
| 6,976,995 B2 | 12/2005 | Mathis et al. |
| 7,048,754 B2 | 5/2006 | Martin et al. |
| 7,179,282 B2 | 2/2007 | Alferness et al. |
| 7,214,344 B2 | 5/2007 | Carpentier et al. |
| 7,226,467 B2 | 6/2007 | Lucatero et al. |
| 7,288,097 B2 | 10/2007 | Seguin |
| 7,311,729 B2 | 12/2007 | Mathis et al. |
| 7,316,708 B2 | 1/2008 | Gordon et al. |
| 7,351,260 B2 | 4/2008 | Nieminen et al. |
| 7,464,712 B2 | 12/2008 | Oz et al. |
| 7,503,931 B2 | 3/2009 | Kowalsky et al. |
| 7,530,253 B2 | 5/2009 | Spenser et al. |
| 7,563,267 B2 | 7/2009 | Goldfarb et al. |
| 7,585,321 B2 | 9/2009 | Cribier |
| 7,604,646 B2 | 10/2009 | Goldfarb et al. |
| 7,608,091 B2 | 10/2009 | Goldfarb et al. |
| 7,655,015 B2 | 2/2010 | Goldfarb et al. |
| 7,666,204 B2 | 2/2010 | Thornton et al. |
| 7,674,287 B2 | 3/2010 | Alferness et al. |
| 7,682,369 B2 | 3/2010 | Seguin |
| 7,736,388 B2 | 6/2010 | Goldfarb et al. |
| 7,780,723 B2 | 8/2010 | Taylor |
| 7,828,841 B2 | 11/2010 | Mathis et al. |
| 7,828,842 B2 | 11/2010 | Nieminen et al. |
| 7,837,728 B2 | 11/2010 | Nieminen et al. |
| 7,837,729 B2 | 11/2010 | Gordon et al. |
| 7,846,203 B2 | 12/2010 | Cribier |
| 7,857,846 B2 | 12/2010 | Alferness et al. |
| 7,895,876 B2 | 3/2011 | Spenser et al. |
| 7,914,569 B2 | 3/2011 | Nguyen et al. |
| 7,955,384 B2 | 6/2011 | Rafiee et al. |
| 8,006,594 B2 | 8/2011 | Hayner et al. |
| 8,057,540 B2 | 11/2011 | Letac et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,226,710 B2 | 7/2012 | Nguyen et al. |
| 8,250,960 B2 | 8/2012 | Hayner et al. |
| 8,382,826 B2 | 2/2013 | Taylor |
| 8,449,599 B2 * | 5/2013 | Chau .................. A61F 2/246 623/1.26 |
| 8,591,575 B2 | 11/2013 | Cribier |
| 8,690,936 B2 | 4/2014 | Nguyen et al. |
| 8,790,387 B2 | 7/2014 | Nguyen et al. |
| 9,061,119 B2 | 6/2015 | Le et al. |
| 9,301,840 B2 | 4/2016 | Nguyen et al. |
| 9,301,841 B2 | 4/2016 | Nguyen et al. |
| 9,339,384 B2 | 5/2016 | Tran et al. |
| 9,393,110 B2 | 7/2016 | Levi et al. |
| 2005/0137682 A1 * | 6/2005 | Justino ................ A61F 2/2418 623/2.14 |
| 2006/0195183 A1 * | 8/2006 | Navia ................. A61F 2/2418 623/2.11 |
| 2008/0071361 A1 | 3/2008 | Tuval et al. |
| 2008/0183273 A1 * | 7/2008 | Mesana ............... A61F 2/2433 623/1.11 |
| 2010/0036479 A1 * | 2/2010 | Hill .................... A61F 2/2457 623/1.26 |
| 2012/0078353 A1 * | 3/2012 | Quadri ................ A61F 2/2436 623/2.11 |
| 2014/0350660 A1 * | 11/2014 | Cocks ................. A61F 2/2418 623/1.16 |
| 2015/0265400 A1 * | 9/2015 | Eidenschink ........ A61F 2/2418 623/2.38 |
| 2016/0081799 A1 * | 3/2016 | Leo .................... A61F 2/2418 623/2.11 |
| 2016/0113764 A1 * | 4/2016 | Sheahan ............. A61F 2/2418 623/2.17 |

OTHER PUBLICATIONS

Sorajja et al., "A novel method of percutaneous mitral valve repair for ischemic mitral regurgitation," JACC: Cardiovascular Interventions, vol. 1, No. 6, pp. 663-672, 2008.

Sack et al., "Percutaneous transvenous mitral annuloplasty," Circulation: Cardiovascular Interventions, vol. 2, No. 4, pp. 277-284, 2009.

International Search Report in relation to corresponding International Application No. PCT/CA2018/050178, dated Aug. 29, 2019.

Edwards, "Edwards SAPIEN 3 Transcatheter Heart Valve with the Edwards Certitude Delivery System: Instructions for Use", Edwards Lifesciences Corporation, Irvine, USA, 69 pages, May 2017.

Edwards, "Edwards SAPIEN 3 Transcatheter Heart Valve with the Edwards Commander Delivery System: Instructions for Use", Edwards Lifesciences Corporation, Irvine, USA, 71 Pages, May 2017.

Medtronic, "CoreValve System: Instructions for Use", Medtronic, Inc., Minneapolis, USA, 48 Pages, 2014.

Mitraclip, "Mitraclip Clip Delivery System: Instructions for Use", Evalve, Inc., Menlo Park, USA, 54 Pages, 2013.

Piazza et al., "Transcatheter Mitral Valve Repair for Functional Mitral Regurgitation: Coronary Sinus Approach", Journal of Interventional Cardiology, vol. 20, No. 6, Blackwell Publishing, Inc., pp. 495-508, 2007.

Harnek et al., "Transcatheter implantation of the monarc coronary sinus device for mitral regurgitation: 1-year results from the evolution phase i study (clinical evaluation of the edwards lifesciences percutaneous mitral annuloplasty system for the treatment of mitral regurgitation)," JACC: Cardiovascular Interventions, vol. 4, No. 1, pp. 115-122, 2011.

Taylor, Metals, In U. Sigwart (Ed.), Endoluminal stenting, W.B. Saunders Company Ltd, London (1996), pp. 28-33.

Cardarelli, Ferrous metals and their alloys, Materials handbook, Springer London Limited, London (2000), pp. 20-21.

Haudrechy et al., Nickel release from 304 and 316 stainless steels in synthetic sweat. Comparison with nickel and nickel-plated metals. Consequences on allergic contact dermatitis, Corros Sci, 35 (1-4) (1993), pp. 329-336.

(56) References Cited

OTHER PUBLICATIONS

Koster et al., Nickel and molybdenum contact allergies in patients with coronary in-stent restenosis, Lancet, 356 (9245) (2000), pp. 1895-1897.
Sumita et al., Durability of metallic implant materials, S.H. Teoh (Ed.), Engineering materials for biomedical applications, World Scientific Publishing Co, Singapore (2004), pp. 2-1 to 2-31.
Stoeckel et al., "Self-expanding nitinol stents: material and design considerations", European Radiology 14(2): 292-301 (2004).
Park et al. (Eds.), Biomaterials principles and applications, CRC Press, Boca Raton (2003), Chapter 1, "Metallic Biomaterials", pp. 1-20.
Davis, Metallic materials, Handbook of medical devices, ASM International, Materials Park (2003), Chapter 3, "Metallic Materials", pp. 21-50.
Trepanier et al., Corrosion resistance and biocompatibility of passivated NiTi, L.H. Yahia (Ed.), Shape memory Implants, Springer, New York (2000), pp. 35-45.
Schurmann et al., Experimental arterial stent placement. Comparison of a new nitinol stent and wallstent, Invest Radiol, 30 (7) (1995), pp. 412-420.
Adams et al., "Comparison of 15 different stents in superficial femoral arteries by high resolution MRI ex vivo and in vivo", J Magn Reson Imag, 22 (1) (2005), pp. 125-135.
Bettini et al., "Nature of Current Increaase for a CoCrMo Alloy: "Transpassive" Dissolution vs. Water Oxidation", Int. J. Electrochem. Sci. 2013, 8, 11791-11804.
Zimmermann et al., Origins of the Selective Cr Oxidation in CoCr Alloy Surfaces, J. Pjus. Chem. Lett. 2010, 1, 2343-2348.
Carek et al., "Mechanical Properties of Co—Cr Alloys for Metal Base Framework", Int. J. Prosthodont. Restor. Dent. 2011, 1(1): 13-19.

Devine et al., Cast vs. Wrought Cobalt-Chromium Surgical Implant Alloys, J. Biomed. Mater. Res. 1975, 9, 151-167.
Ratner et al. (Eds.), Biomaterials science an introduction to materials in medicine (2nd ed), Elsevier Academic Press, San Diego (2004), pp. 137-153.
Briguori et al., In-stent restenosis in small coronary arteries: impact of strut thickness, J Am Coll Cardiol, 40 (3) (2002), pp. 403-409.
Kastrati et al., "Intercoronary stenting and angiographic results: strut thickness effect on restenosis outcome (ISAR-Stereo) Trial", Circulation, 103 (23) (2001), pp. 2816-2821.
Rittersma et al., Impact of strut thickness on late luminal loss after coronary artery stent placement, Am J Cardiol, 93 (4) (2004), pp. 477-480.
Kereiakes et al., Usefulness of a cobalt chromium coronary stent alloy, Am J Cardiol, 92 (4) (2003), pp. 463-466, Am J Cardiol, 92 (4) (2003), pp. 463-466.
Klocke et al., Magnetic field interactions of orthodontic wires during magnetic resonance imaging (MRI) at 1.5 Tesla, J Orofac Orthop, 66 (4) (2005), pp. 279-287.
Young et al., "Simulation Based Design and Evaluation of a Transcatheter Mitral Heart Valve Frame", Journal of Medical Devices, 2012, 6(3): 31005-31012.
Pelton et al., "Fatigue testing of diamond-shape specimens", In Pelton et al. (Eds.), Proceedings of the International Conference on Shape Memory and Superelastic Technologies, Pacific Grove, CA: SMST, 2003, pp. 293-302.
Gong et al., "Fatigue to fracture: an informative, fast, and reliable approach for assessing medical implant durability", J ASTM Int, 2009, 6(7): 1-10.
Esterhuyse et al., "Application of the finite element method in the fatigue life prediction of a stent for a percutaneous heart valve", J Mech Med Biol, 2011, 12(1): 1250007-1 to 1250007-18.

\* cited by examiner

TRANSCATHETER HEART VALVE APPARATUS FOR CALCIFIC MITRAL STENOSIS

FIELD

This disclosure relates generally to transcatheter heart valves, and more specifically to transcatheter heart valves for placement in the mitral valve.

BACKGROUND

In a human heart, the mitral valve allows one-way blood flow from the left atrium (the chamber receiving oxygenated blood from the lungs) to the left ventricle (the main pumping chamber of the heart) to assist in distributing oxygenated blood throughout the body.

The mitral valve may become narrow in certain disease states, causing restriction of free blood flow from the left atrium to the left ventricle, which is a condition referred to as mitral stenosis. The inadequate opening of the mitral valve in a patient with mitral stenosis typically results in decreased forward blood flow from the heart to the body, and may also result in increased blood volume and/or increased blood pressure in the left atrium and/or in the lungs. This problem often manifests in breathing difficulties and cardiac dysfunction for the patient, affecting their overall health and longevity.

Mitral stenosis is characterized by tissue fibrosis and calcification in the mitral annulus, causing the mitral annulus to become thicker and harder, i.e. losing normal cardiac tissue pliability. In addition, the leaflets of the mitral valve may experience a loss of normal flexibility and movement. Also, the degenerative process may extend to the chordae tendineae and the associated portion of the mitral valve that is important for the mitral valve to perform its normal function.

Mitral stenosis may result from late complications of rheumatic fever (typically in younger and middle age adults), or from degenerative heart disease (typically in older adults). For example, mitral stenosis affecting people older than 60 years of age is often a result of degenerative disease whose symptoms include heavy calcification and thickening of the mitral valve annulus and leaflets. This condition may be referred to more specifically as "degenerative and calcific mitral stenosis".

Mitral stenosis is commonly treated by valvuloplasty, where a balloon attached to the tip of a catheter is advanced and inflated across the mitral valve to prop open the valve leaflets. Certain cases of mitral stenosis in which the mitral valve is not suitable for valvuloplasty are treated with open heart surgery, where the diseased valve is removed and a new porcine, bovine, or mechanical heart valve is implanted. However, degenerative or calcific mitral stenosis, the predominant pathology in the elderly, is not suitable for valvuloplasty due to structural changes in the mitral valve anatomy with inadequate response to balloon dilatation. In addition, many patients are at high risk of surgery due to associated medical conditions, presenting a major challenge for management.

SUMMARY

In accordance with a broad aspect, there is provided an apparatus for placement in a mitral heart valve, the apparatus comprising: an annular body made from a first material and having first and second spaced apart ends, a longitudinally extending axis, and an interior volume extending from the first end to the second end; a plurality of first anchor members made from a second material and extending from the first end of the annular body; and at least two paddles made from the second material and extending from the second end of the annular body; wherein, in a compressed state, the annular body has a first diameter, the plurality of first anchor members extend substantially longitudinally from the first end of the annular body, and the at least two paddles extend substantially longitudinally from the second end of the annular body, and wherein, in an expanded state, the annular body has a second diameter larger than the first diameter, the plurality of first anchor members extend longitudinally and radially outward from the first end of the annular body for engaging an upstream portion of a mitral valve annulus to resist displacement of the annular body towards a left ventricle, and the at least two paddles extend longitudinally and radially outward from the second end of the annular body for engaging chordae tendineae.

In at least one embodiment, the apparatus further comprises a plurality of second anchor members made from the second material and extending from the second end of the annular body, wherein, in the compressed state, the plurality of second anchor members extend substantially longitudinally from the first end of the annular body, and wherein, in the expanded state, the plurality of second anchor members extend longitudinally and radially outward from the second end of the annular body for engaging a downstream portion of a mitral valve annulus to resist displacement of the annular body towards a left atrium.

In at least one embodiment, an average length of the plurality of first anchor members is larger than an average length of the plurality of second anchor members.

In at least one embodiment, at least some of the plurality of second anchor members are hook-shaped.

In at least one embodiment, the plurality of first anchor members are welded to the annular body, and wherein the at least two paddles are welded to the annular body.

In at least one embodiment, the annular body comprises a plurality of diamond shaped openings.

In at least one embodiment, the apparatus further comprises at least two guide projections for engaging at least one guide wire for facilitating placement of the apparatus within the mitral valve annulus in a desired orientation.

In at least one embodiment, the guide projections are provided on the plurality of first anchor members.

In at least one embodiment, the annular body comprises a first portion made from the first material and a second portion made from the second material, wherein the plurality of first anchor members extend from a first end of the second portion, and wherein the at least two paddles extend from a second end of the second portion.

In at least one embodiment, the second portion, the plurality of first anchor members, and the at least two paddles are integrally formed.

In at least one embodiment, the first portion is secured to the second portion by at least one weld.

In at least one embodiment, the apparatus further comprises a fabric material positioned on at least a portion of an outer surface of the annular body.

In at least one embodiment, the fabric material comprises a Dacron fabric.

In at least one embodiment, the apparatus further comprises at least two valve leaflets positioned in the interior volume and configured such that, in the expanded state, blood flow through the interior volume towards the first end is impeded.

In at least one embodiment, the annular body is configured to be expanded from the compressed state to the expanded state using a balloon catheter.

In at least one embodiment, the first material is a cobalt chromium alloy and the second material is shape-memory alloy.

In at least one embodiment, the second material is a nitinol alloy.

In at least one embodiment, the first material is a shape memory alloy, and the second material is the same shape-memory alloy as the first material.

In at least one embodiment, the first material is a nitinol alloy.

In accordance with another broad aspect, there is provided an apparatus for placement in a mitral heart valve, the apparatus comprising: a first annular body member having a longitudinally extending axis, a plurality of deployable anchor members provided at a first end of the body member, and at least two deployable paddles provided at a second end of the annular body; and a second annular body member secured to the first annular body member between the plurality of deployable anchor members and the at least two deployable paddles; wherein the first annular body member is made of a shape memory alloy, and the second annular body member is made of one of a cobalt chromium alloy and a shape memory alloy.

In at least one embodiment, the first annular body member is made of a nitinol alloy, and wherein the second annular body member is made of the nitinol alloy.

In accordance with another broad aspect, there is provided an apparatus for placement in a mitral heart valve, the apparatus comprising: an annular body comprising one or more stent struts having a stent strut thickness, the annular body having an interior volume extending from the first end to the second end and a longitudinally extending axis; a plurality of deployable first anchor members provided at the first end of the annular body, the plurality of deployable first anchor members having an anchor member thickness in a radial direction that is less than the stent strut thickness; and at least two deployable paddles provided at the second end of the annular body, the at least two deployable paddles having a paddle thickness in a radial direction that is less than the stent strut thickness; wherein, in a compressed state, the annular body has a first diameter, the plurality of deployable first anchor members extend substantially longitudinally from the first end of the annular body, and the at least two deployable paddles extend substantially longitudinally from the second end of the annular body, and wherein, in an expanded state, the annular body has a second diameter larger than the first diameter, the plurality of first anchor members extend longitudinally and radially outward from the first end of the annular body for engaging an upstream portion of a mitral valve annulus to resist displacement of the annular body towards a left ventricle, and the at least two paddles extend longitudinally and radially outward from the second end of the annular body for engaging chordae tendineae.

In at least one embodiment, the apparatus further comprises a plurality of second anchor members extending from the second end of the annular body, wherein, in the compressed state, the plurality of second anchor members extend substantially longitudinally from the first end of the annular body, and wherein, in the expanded state, the plurality of second anchor members extend longitudinally and radially outward from the second end of the annular body for engaging a subvalvular apparatus to resist displacement of the annular body towards a left atrium.

In at least one embodiment, an average length of the plurality of first anchor members is larger than an average length of the plurality of second anchor members.

In at least one embodiment, at least some of the plurality of second anchor members are hook-shaped.

In at least one embodiment, the annular body comprises a plurality of diamond shaped openings.

In at least one embodiment, the apparatus further comprises at least two guide projections for engaging at least one guide wire for facilitating placement of the apparatus within the mitral valve annulus in a desired orientation.

In at least one embodiment, the guide projections are provided on the plurality of first anchor members.

In at least one embodiment, the annular body, the plurality of first anchor members, and the at least two paddles are made from the same material.

In at least one embodiment, the second portion, the plurality of first anchor members, and the at least two paddles are integrally formed.

In at least one embodiment, the apparatus further comprises a fabric material positioned on at least a portion of an outer surface of the annular body.

In at least one embodiment, the fabric material comprises a Dacron fabric.

In at least one embodiment, the apparatus further comprises at least two valve leaflets positioned in the interior volume and configured such that, in the expanded state, blood flow through the interior volume towards the first end is impeded.

In at least one embodiment, the anchor member thickness and the paddle thickness are substantially the same.

In at least one embodiment, the stent strut thickness is about 0.5 mm, and the anchor member thickness is about 0.3 mm.

In at least one embodiment, the annular body, the plurality of deployable first anchor members, and the at least two deployable paddles are made from a shape-memory alloy.

In at least one embodiment, the shape-memory alloy is a nitinol alloy.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
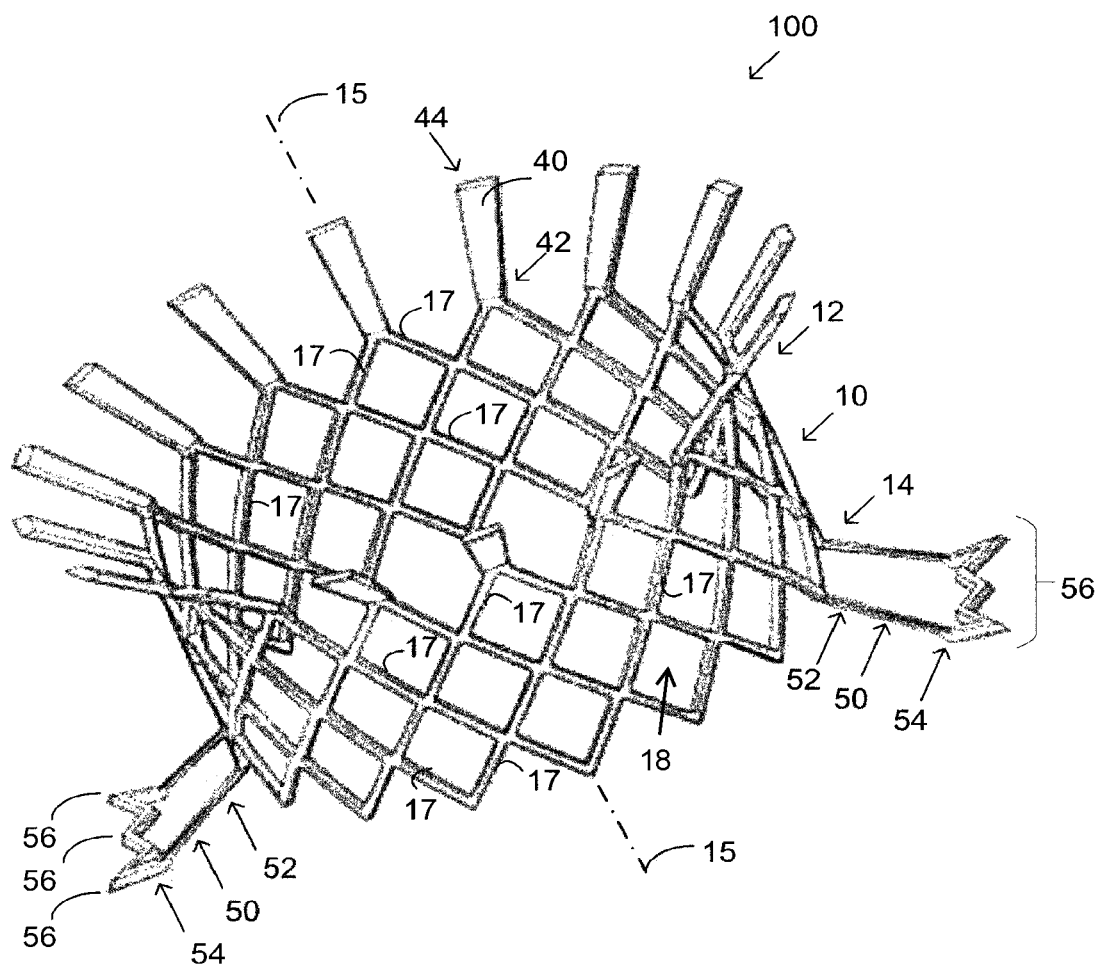
FIG. 1 is a perspective view of an apparatus for use in replacing a mitral heart valve according to an example embodiment.

Further aspects and features of the example embodiments described herein will appear from the following description taken together with the accompanying drawings.

DESCRIPTION OF EXAMPLE EMBODIMENTS

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

The following introduction is provided to introduce the reader to the more detailed discussion to follow. The introduction is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that a method or apparatus disclosed in accordance with the teachings herein may embody any one or more of the features contained herein and that the features may be used in any particular combination or sub-combination that is physically feasible and realizable for its intended purpose.

Transcatheter heart valves (THVs) that have been developed recently include valves made of stent struts that have been crimped and mounted on a catheter tip for implantation in diseased and malfunctioning heart valves. Typically, these THVs have been developed for the management of aortic stenosis, and have been successfully used in patients who are not best suited for open heart surgery for aortic valve replacement. Although some of these THV devices designed for aortic valve disease have been used in the treatment of degenerative mitral stenosis, the success rates have been relatively low. The inventors believe that reasons for these low success rates are thought to include the unique anatomical features of the mitral valve (e.g. as compared with the aortic valve), and/or the specific disease processes that typically affect the mitral valve annulus and the mitral leaflets. Overall, it does not appear that any of the conventional THV devices developed for use in the treatment of aortic stenosis work well for the treatment of mitral stenosis.

Currently available THVs include balloon-expandable designs, which are typically made of stainless steel or cobalt chromium, and self-expanding designs, which are typically made of nitinol alloys. While current THV designs may be suitable for the transcatheter treatment of aortic valve disease, they may not be suitable for the treatment of mitral valve disease.

For example, the inventors have realized that current THV designs may lack adequate radial strength to overcome tissue resistance of the type seen in mitral stenosis. A lack of sufficient radial strength is seen in nitinol based self-expanding THV devices that have been developed for use in patients with mitral insufficiency, as these devices may not have the radial strength to overcome tissue resistance seen in patients with rheumatic or degenerative and calcific mitral stenosis. However, a lack of sufficient radial strength to overcome the tissue resistance that may be present in mitral stenosis may result in incomplete THV expansion and/or malfunction of the valve.

Also, the inventors have realized that current THV designs may lack sufficient anchoring mechanisms for proper implantation in the mitral valve of a patient with mitral stenosis. For example, the inventors have found that current THV designs may provide relatively poor stability in the mitral position due to inadequate anchoring at the mitral annulus, resulting in poor stabilization of the valve at the mitral annulus. Where insufficient stabilization is provided, there may be an increased risk of embolization into the left atrium as a result of ventricular contractions after implantation.

Also, the inventors have found that current THV designs have typically been developed with consideration of aortic valve anatomy, and may not be suitable for proper functioning at the mitral position. For example, when implanted at the mitral position, there may be a significant risk of interaction with the left ventricular outflow tract and obstruction to the blood flow from the left ventricular cavity to the ascending aorta, which can be problematic. For example, a protrusion of the THV in the left ventricular outflow tract may increase the potential for blood flow obstruction.

Also, as the mitral annulus is a dynamic structure, the inventors have found that current designs of THV devices may be poorly suited for placement or implantation in such a structure. For example, current THV designs may provide poor sealing around the mitral annulus, resulting in leaking of blood flow around the implanted THV with inadequate hemodynamic results. Such leaking may be characterized as a residual 'paravalvular leak' due to incomplete THV apposition with the mitral annulus.

Various example embodiments of a mitral-specific apparatus are disclosed according to the teachings herein in which the inventors have considered one or more of these pathophysiological conditions in creating a mitral valve apparatus in an effort to achieve improved results. In particular, the teachings described herein relate to at least one example embodiment of an apparatus and method designed for the treatment of mitral stenosis, and that are directly applicable to the at least one of the unique anatomical and functional challenges of mitral stenosis. For example, the apparatus and methods described herein may be used as a substitution for conventional mitral valve replacement by open heart surgery. However, it will be appreciated that the apparatus and methods disclosed herein may be modified to have other applications.

Embodiments disclosed herein may include one or more features in an effort to address the requirements of a THV for use in the treatment of mitral stenosis. For example, these features include: an overall structure and shape for improved positioning, placement, and anchoring at the mitral annulus; the use of a combination of materials to overcome the tissue resistance of the mitral valve annulus and morphologic characteristic of mitral stenosis as well as to avoid trauma and interaction with other cardiac structures; and the provision of an optional fabric material that may provide improved hemodynamic performance (e.g. absence of blood flow obstruction from the left ventricle to the ascending aorta) and reduced risk of paravalvular leak.

In this respect, the transcatheter heart valve apparatus embodiments for replacing the function of the mitral valve (i.e. by implantation in the annulus of a defective mitral valve) in patients with mitral stenosis as described herein have been created to address one or more of the following objectives: (1) the apparatus is capable of being configured in a crimped or compressed state for e.g. percutaneous delivery through a hole in the vessel leading to the heart or a small hole in the apex of the heart with the aid of delivery catheter; after delivery and positioning in a target location (e.g. across a mitral valve), (2) the apparatus is capable of being configured to an expanded state (e.g. with a balloon catheter and/or thermally actuated shape memory alloy recovery); (3) after delivery and positioning in the target location, the THV valve functions in a one way direction to allow blood flow from a left atrium to a left ventricle, while restricting or preventing blood flow from a left ventricle to a left atrium; (4) after delivery and positioning in the target location, the apparatus has sufficient anchoring to the adjacent tissue to avoid movement and migration during normal heart functioning (e.g. pumping); and, (5) after delivery and positioning in the target location, the apparatus avoids interaction with other cardiac structures (e.g. the left ventricular outflow tract and/or the aortic valve).

Some aspects of one or more of the mitral valve apparatuses described herein that distinguish from known percutaneous valve prostheses include at least one of: (1) a main annular body having sufficient strength (e.g. made from a relatively strong material such as stainless steel or cobalt chromium alloys, and/or having an increased radial thickness) to withstand the forces applied by thickened and/or calcified tissue during normal heart operation; (2) anchor members and paddles extending from the ends of the main annular body that are either made from a different material (e.g. a shape memory alloy such as nitinol) than the main annular body, or made from the same material as the main annular body (e.g. nitinol) but with a thinner radial thickness than the main annular body, to provide flexibility in shape for deployment and to accommodate motion (i.e. the ends of the main annular body slightly move) while the heart is beating; and, (3) anchor members extending from one end of the main annular body for engaging an upstream portion of a mitral valve annulus to resist displacement of the main annular body towards a left ventricle, and paddles extending from the other end of the main body for engaging chordae tendineae to assist in anchoring of the device to the left aorta.

Characteristics that were considered in the creation of the embodiments of the mitral valve apparatus according to the teachings herein include one or more of: (1) sufficient compressability or crimpability for mounting on a deployment device such as, but not limited to, a balloon catheter supported by a guide wire, for example; (2) providing a low profile in a compressed state to facilitate introduction into a patient via minimally invasive means (e.g. through a vascular structure (e.g. an artery or a vein), or direct cardiac puncture, or during open heart surgery via left atrial access under direct visual guidance); (3) sufficient flexibility when in a compressed state to pass through the normal human vascular tortuosity during deployment; (4) for the main annular body, the optional ability to undergo plastic deformation (e.g. via balloon expansion) and then maintain a required size after being deployed; (5) for the anchor members and paddles, sufficient elasticity to be compressed for delivery and then expanded in the target area; (6) an adequate expandability ratio (e.g. after insertion into the target area, the apparatus undergoes sufficient expansion (e.g. via balloon expansion or shape-memory recovery) to conform to the surrounding tissue; (7) sufficient radial strength and low recoil after implantation (e.g. the stent overcomes the forces imposed by the surrounding cardiac structures and does not collapse or significantly compress); (8) sufficient radiopacity/magnetic resonance imaging (MRI) compatibility (e.g. to assist clinicians in detecting the location of the stent in vivo and to safely function during routine radio-diagnostic procedures; and (9) thrombotic resistance (e.g. the valve material should be compatible with implantation in a human body and not promote excessive blood clot formation (e.g. platelet adhesion and/or deposition) that cannot be managed with typical therapies (e.g. administration of blood thinners)).

Figure 5:
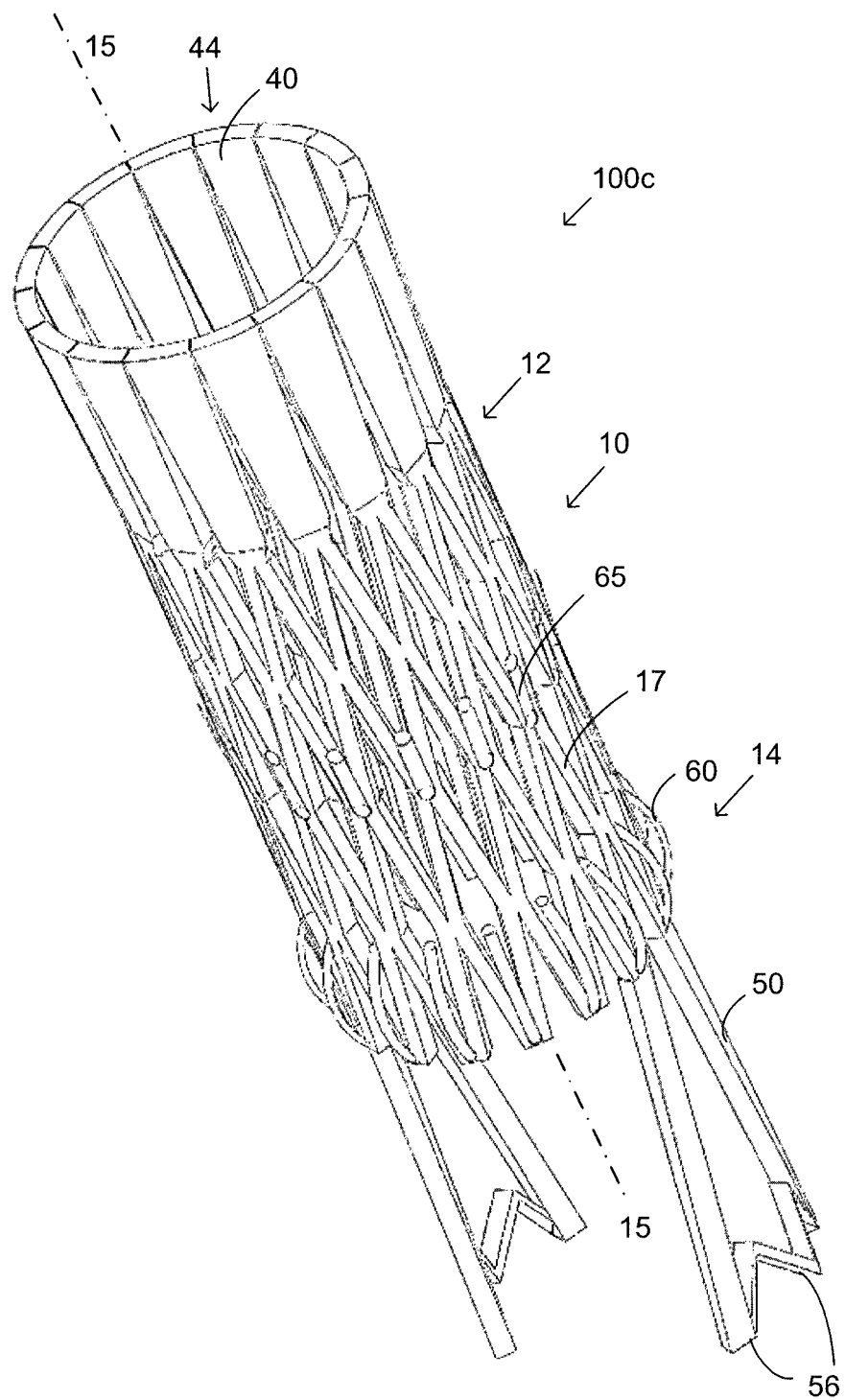
FIG. 5 is a perspective view of the apparatus of FIG. 4 in a compressed state.
Figure 9:
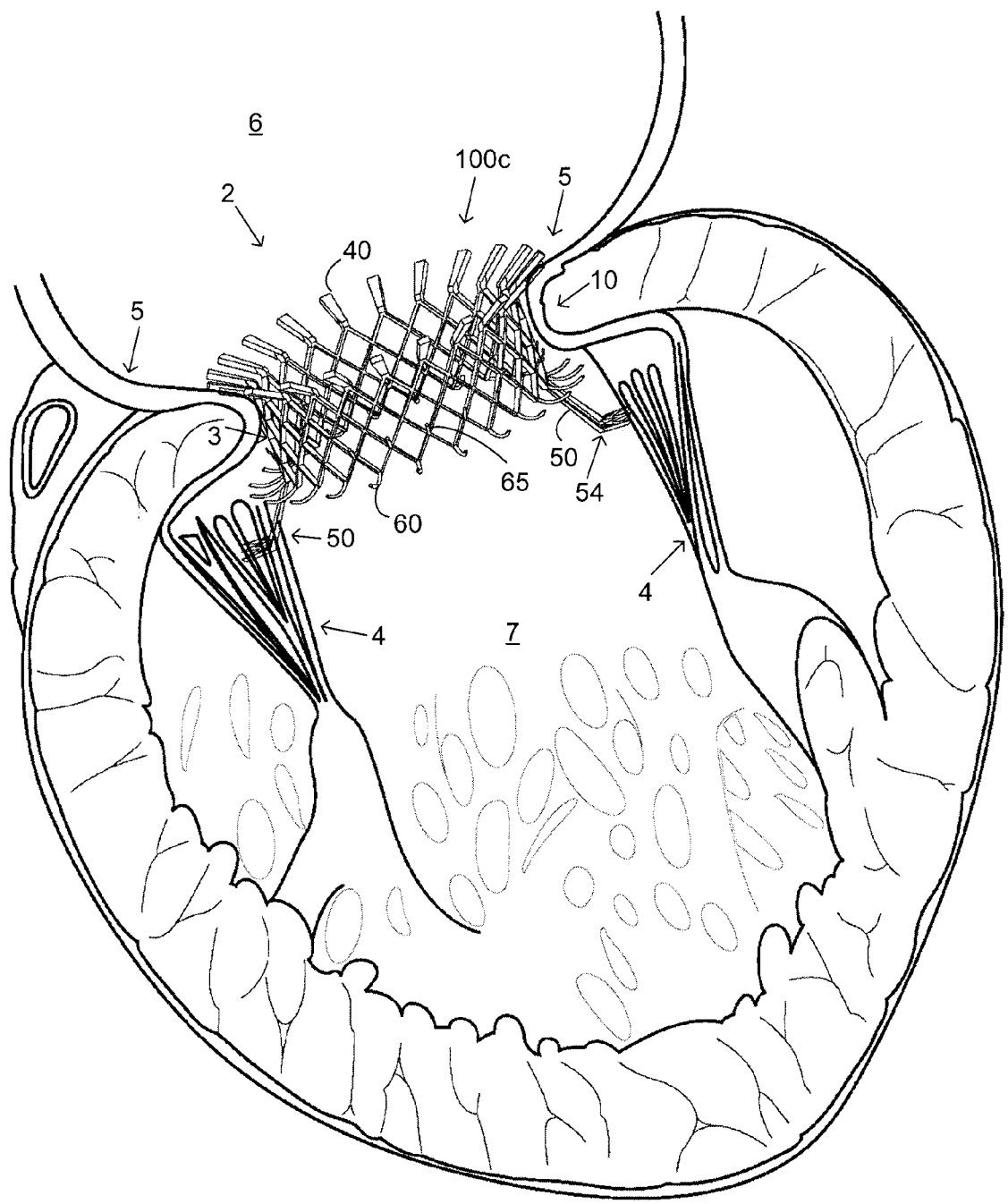
FIG. 9 is a perspective view the apparatus of FIG. 4 positioned in a mitral valve annulus of a heart, which is shown in partial section.

Referring now to FIG. 1, illustrated therein is an apparatus 100 for use in replacing a mitral heart valve, which may also be referred to as a transcatheter heart valve (THV) frame or stent 100. The apparatus 100 includes: a main annular body or frame, shown generally as 10, for positioning in a mitral annulus and for supporting two or more mitral valve leaflets; a plurality of anchor members 40 extending from one end of the annular body 10, for engaging an upstream portion of a mitral valve annulus to resist displacement of the annular body 10; and two other anchors or paddles 50 extending from the other end of the annular body 10, for engaging chordae tendineae (see e.g. FIG. 9, illustrating paddles 50 engaging chordae tendoneae 4). In FIG. 1, the apparatus 100 is illustrated in an expanded state. In FIG. 5, an alternative embodiment of an apparatus 100c is illustrated in a crimped or compressed state.

Returning to FIG. 1, the main annular body 10 has a first end 12, a second end 14, and a longitudinal axis 15. Preferably, the main annular body 10 comprises a number of stent struts 17 (only some of which are labelled for ease of illustration). In some embodiments, as shown in FIG. 1, the stent struts 17 may be arranged so that a plurality of diamond shaped openings 18 are provided. A plurality of anchor members 40 (only one of which is labelled for ease of illustration) extend longitudinally from the first end 12 of the annular body 10. The anchor members 40 each have a proximal end 42 adjacent to the first end 12 of the annular body 10, and a distal end 44. As shown in FIG. 1, in an expanded state the anchor members 40 extend longitudinally and radially outward from the first end 12 of the annular body 10. As with apparatus 100c illustrated in FIG. 9, when the apparatus 100 is positioned in a mitral annulus, the anchor members 40 are configured to engage an upstream portion of the mitral valve annulus (see e.g. FIG. 9, illustrating anchor members 40 engaging the superior surface 5 of the mitral orifice), and thereby resist displacement of the apparatus 100 downwards towards a left ventricle.

As with apparatus 100c shown in FIG. 5, in a crimped or compressed state, the anchor members 40 extend substantially longitudinally from the first end 12 of the annular body 10, which may facilitate the insertion of apparatus 100 into a mitral annulus.

Figure 14:
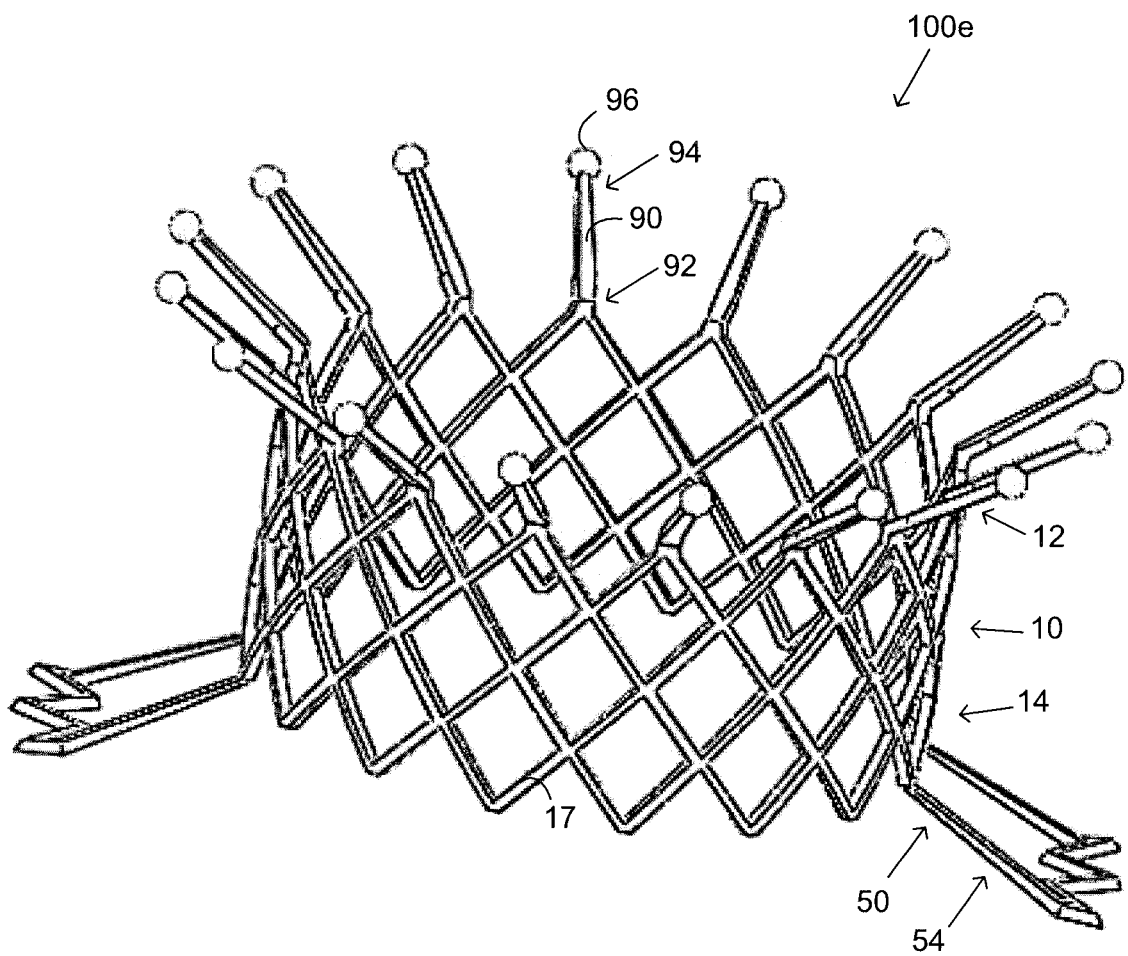
FIG. 14 is a perspective view of an apparatus for use in replacing a mitral heart valve according to another example embodiment.

As illustrated in FIG. 1, the anchor members 40 preferably have a broad, planar shape, in order to stabilize the apparatus 100 in the mitral annulus and/or to prevent dislocation of the apparatus 100 (e.g. to resist motion of the apparatus 100 towards the left ventricle). It will be appreciated that anchor members 40 having different shapes may be alternatively (or additionally) provided. For example, FIG. 14 illustrates an alternative embodiment 100e that includes an alternative design for anchor members 90, in which pin-head shaped projections 96 are provided at distal ends 94. Alternatively, or additionally, the anchor members for each of the different apparatuses may each have a tapered profile.

Returning to FIG. 1, additional anchors or paddles 50 extend longitudinally from the second end 14 of the annular body 10. The paddles 50 each have a proximal end 52 adjacent the second end 14 of the annular body 10, and a distal end 54. As shown in FIG. 1, in an expanded state, the paddles 50 extend longitudinally and radially outward from the second end 14 of the annular body 10. As with the apparatus 100c illustrated in FIG. 9, when the apparatus 100 is positioned in a mitral annulus, the paddles 50 are configured to engage chordae tendineae, and thereby resist displacement of the apparatus 100 towards a left atrium, and/or resist rotation of apparatus 100 about its longitudinal axis 15 during use. Alternatively, or additionally, the paddles 50 may interact with the papillary muscles of a mitral valve for improved anchoring (e.g. to resist motion of the apparatus 100 towards the left atrium).

Preferably, the paddles 50 each have one or more prongs or tines 56 provided at distal end 56, for facilitating engagement of the paddles with chordae tendineae. Also, while two paddles are illustrated, it will be appreciated that three or four or more paddles 50 may be provided in alternative embodiments.

As shown in FIG. 5, in a crimped or compressed state, paddles 50 extend substantially longitudinally from the second end 14 of the annular body 10, which may facilitate the insertion of the apparatus 100 into a mitral annulus during deployment.

The annular body 10, anchors 40, and paddles 50 are preferably made from one or more metals or metallic alloys. Mechanical properties of select metals/alloys commonly used in making stents and other implantable devices are shown in Table 1.

TABLE 1

| Metal/Alloy | Elastic modulus (GPa) | Yield strength (MPa) | Tensile strength (MPa) | Density (g/cm³) |
| --- | --- | --- | --- | --- |
| 316L stainless steel (ASTM F138 and F139; annealed) | 190 | 331 | 586 | 7.9 |
| Nitinol | 83 (Austenite phase) 28-41 (Martensite phase) | 195-690 (Austenite phase) 70-140 (Martensite phase) | 895 | 6.7 |
| Cobalt-chromium (ASTM F90) | 210 | 448-648 | 951-1220 | 9.2 |

The annular body 10 is preferably made from a relatively high strength material, such as a cobalt chromium alloy. An annular body made of such a material may have one or more advantages when the apparatus 100 is deployed in a mitral annulus. For example, use of such a material may provide the apparatus 100 with a relatively high radial strength once expanded, while still being balloon expandable. Also, the relatively high strength may allow the apparatus 100 to open the hard calcified tissue in the opening of mitral valve and resist the tissue inward pressure. In contrast, existing THVs (which are typically made from softer alloys) may be more likely to deform when positioned in a mitral annulus due to the pressure of the calcified tissue.

Cobalt-chrome or cobalt-chromium (Co—Cr) is a metal alloy of cobalt and chromium. Co—Cr has a very high specific strength. Co—Cr alloys show high resistance to corrosion due to the spontaneous formation of a protective passive film composed of mostly $Cr_2O_3$, and minor amounts of cobalt and other metal oxides on the surface. As its wide application in biomedical industry indicates, Co—Cr alloys are well known for their biocompatibility. Biocompatibility also depends on the protective film and how this oxidized surface interacts with its physiological environment. Good mechanical properties that are similar to stainless steel are a result of a multiphase structure and precipitation of carbides, which increase the hardness of Co—Cr alloys tremendously. The hardness of Co—Cr alloys varies ranging from 550-800 MPa, and the tensile strength varies ranging from 951 to 1220 MPa. Moreover, tensile and fatigue strength increases significantly as they are heat-treated. Co—Cr alloy has also been widely used in the manufacture of stent and other surgical implants as Co—Cr alloy demonstrates excellent biocompatibility with blood and soft tissues as well. Co—Cr alloys, which conform to ASTM standards F562 and F90, have been used in dental and orthopedic applications for decades and recently have been used for making stents. These alloys have excellent radial strength because of their high elastic modulus (see e.g. Table 1). The thickness of the struts or structural members of the annular body is an important structural feature of a stent; hence, the ability to make ultra-thin struts with increased strength using these alloys is one of their main attractions. In addition to this, these materials are radiopaque and MRI-compatible.

Another metal material that is commonly used for stents is 316 L stainless steel ["316L SS"]. It has well-suited mechanical properties (see e.g. Table 1) and excellent corrosion resistance (carbon content <0.030 wt %). However, clinical limitations of using 316L SS include its ferromagnetic nature (60-65 wt % pure Fe), which makes 316L SS incompatible with Magnetic Resonance Imaging (MRI). Also, the relatively low density of 316L SS results in it being a somewhat poorly visible fluoroscopic material, which may result in the implantation of an 316L SS apparatus using fluoroscopic guidance being somewhat more difficult than the guidance and/or implantation of a more fluoroscopically visible material. Also, biocompatibility is an issue with bare stainless steel stents. The weight percentage of nickel, chromium, and molybdenum in 316L SS are 12, 17, and 2.5, respectively. Allergic reactions to the release of nickel can occur among stainless steel implants. In particular, the release of nickel, chromate, and molybdenum ions from stainless steel stents may trigger local immune response and inflammatory reactions, which may induce intimal hyperplasia and in-stent restenosis.

The anchors 40 and paddles 50 are preferably made from self-expanding and/or shape memory alloys, such as nickel titanium (NiTi) shape memory alloys. Nickel titanium (also known as nitinol) is a shape-memory alloy of nickel and titanium that has the ability to be deformed at lower temperatures, but regain its original shape at higher temperatures (e.g. body temperature). When the anchors 40 and paddles 50 are made of such a material they may have one or more advantages when the apparatus 100 is deployed in a mitral annulus. For example, the anchors 40 and paddles 50 may be configured to expand to their expanded position after deployment with little or no physical manipulation (e.g. by a surgeon), which may cause better anchorage of the valve apparatus 100 in the target location.

Nitinol constitutes between 49.5-57.5% nickel and the remainder being titanium. It is used for fabricating self-expanding stents mainly because of its shape memory effect. Self-expanding stents have a smaller diameter at room temperature and expand to their preset diameter at body temperature. NiTi is plastically deformed at room temperature (martensitic phase) and can be crimped onto a delivery system (e.g. a balloon-tipped catheter). After implantation this material regains its original shape (already memorized austenite phase according to the diameter of the target vessel) and conforms to the vessel wall because of the increase in temperature inside the body. The maximum strain recovery is 8.5% after plastic deformation. NiTi also has suitable mechanical properties (see e.g. Table 1). While the corrosion resistance of NiTi is actively debated, the literature generally portrays NiTi as a corrosion resistant material. NiTi stents are not adequately visible by fluoroscopy and while this may be an issue, MRI can sufficiently visualize a NiTi stent.

In some embodiments, the annular body 10 is made of a first material (e.g. Co—Cr), and the anchors 40 and paddles 50 are made of a second material (e.g. nitinol) and attached to the annular body 10 by welding (e.g. laser welding).

Figure 2:
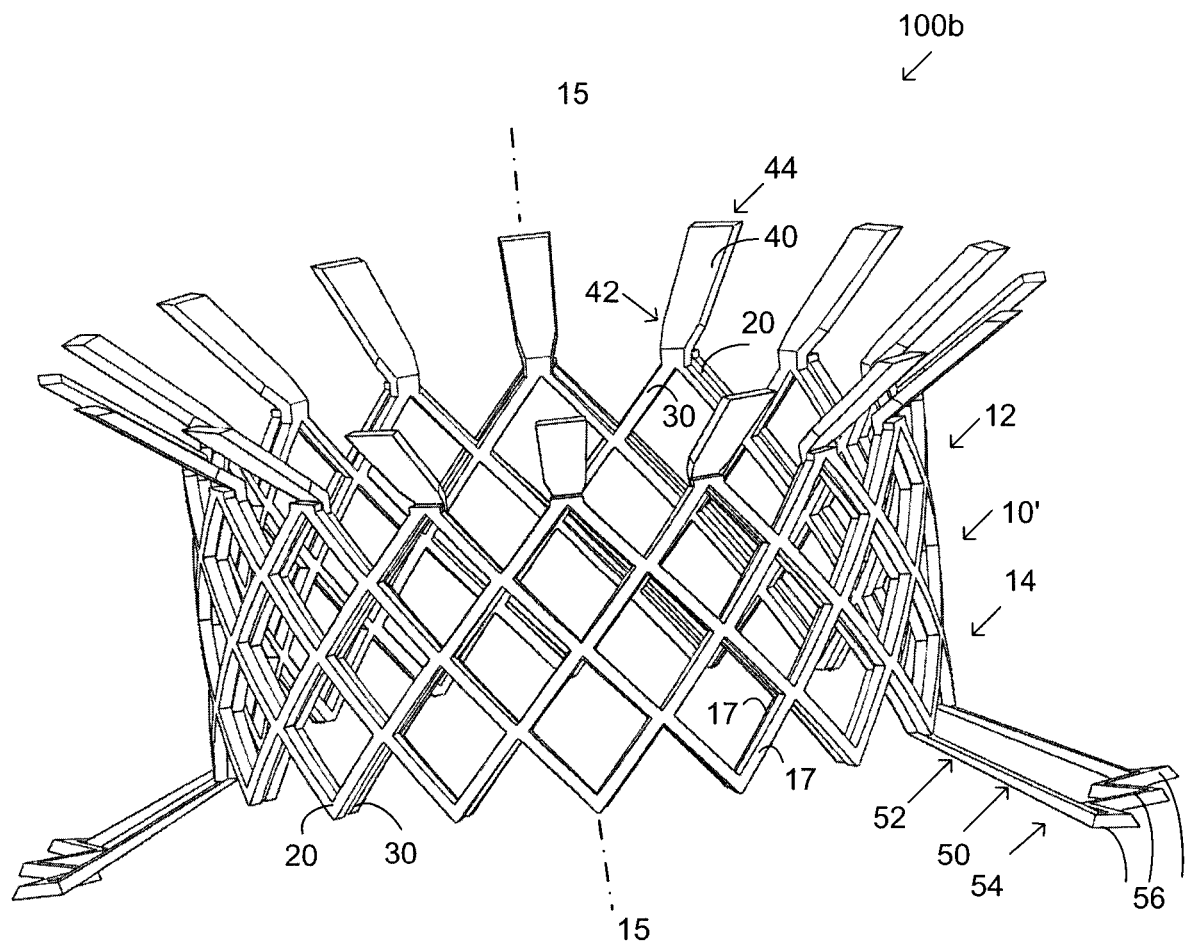
FIG. 2 is a perspective view of an apparatus for use in replacing a mitral heart valve according to another example embodiment.
Figure 3:
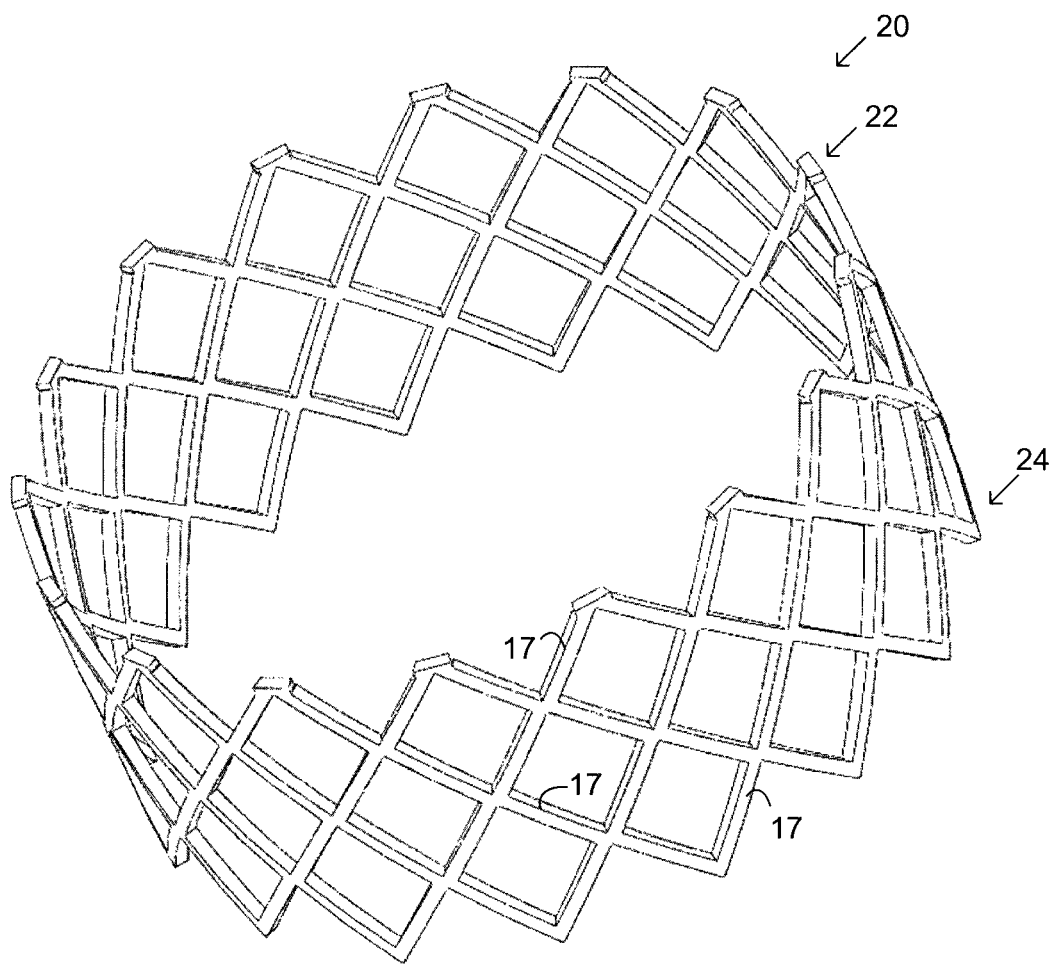
FIG. 3 is a perspective view of an annular body of the apparatus of FIG. 2.

In alternative embodiments, such as apparatus 100b illustrated in FIG. 2, the apparatus 100b includes a first component or layer 20 comprising a primary annular body (see e.g. FIG. 3), and a second component or layer comprising anchors 40, paddles 50, and a secondary annular body 30.

In some embodiments, the first component or layer 20 may be made of a stronger first material (e.g. Co—Cr), and the second component or layer may be made of a weaker second material (e.g. nitinol).

Alternatively, the first component and the second component may be made from the same material (e.g. a shape memory alloy such as nitinol). Where the first component and the second component are made from the same material, the first component may be configured to have a higher strength than the second component by varying the size and/or shape of the components. For example, a first component 20 may be provided with stent struts 17 that are thicker than stent struts of the secondary annular body 30.

The primary and secondary annular bodies 20, 30 may be secured to each other using one or more spot welds, one or more sutures or other mechanical securement methods, or by any other suitable mechanism. As illustrated in FIG. 2, the primary annular body 20 is preferably positioned exterior to the secondary annular body 30, although the primary annular body 20 may, in alternative embodiments, be positioned at the interior of the secondary annular body 30.

Figure 4:
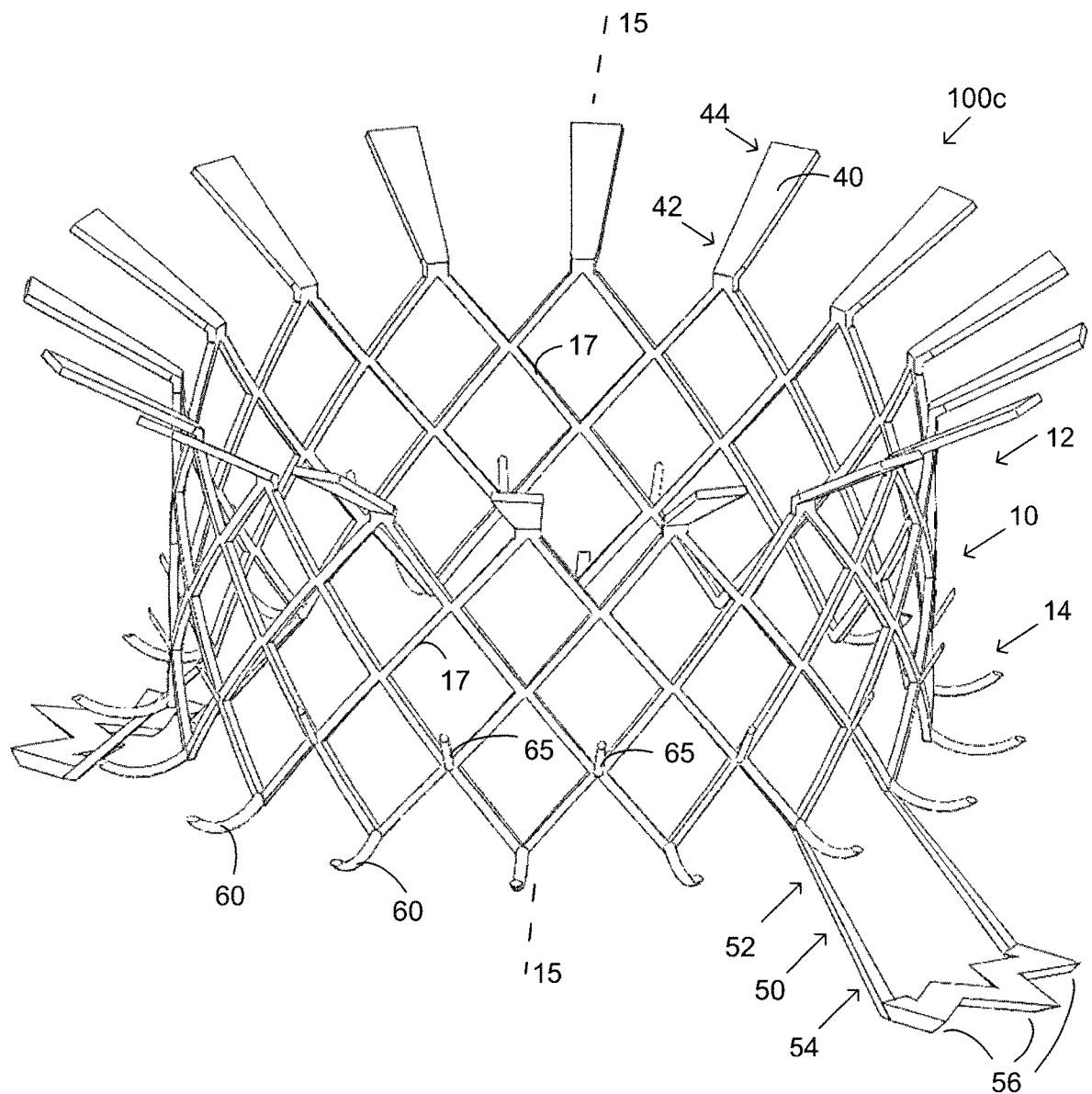
FIG. 4 is a perspective view of an apparatus for use in replacing a mitral heart valve according to another example embodiment.

Optionally, as illustrated in e.g. FIG. 4, an apparatus 100c may include a plurality of second anchor members or hooks 60 extending longitudinally from the second end 14 of annular body 10. As shown, in an expanded state the hooks 60 extend longitudinally and radially outward from the second end 14 of the annular body 10. As illustrated in FIG. 9, when the apparatus 100c is positioned in a mitral annulus, the hooks 60 are configured to engage a subvalvular surface to resist displacement of the annular body 10 (e.g. to resist motion of the apparatus towards the left atrium).

Optionally, as illustrated in e.g. FIG. 4, apparatus 100c may alternatively, or additionally, include a plurality of anchor members or hooks 65 extending radially from the annular body 10. As shown, in an expanded state the hooks 65 extend radially outward from the annular body 10 and are preferably angled longitudinally towards the first end 12. As illustrated in FIG. 9, when the apparatus 100c is positioned in the mitral annulus 2 between a left atrium 6 and a left ventricle 7, the hooks 65 are configured to engage (e.g. penetrate) the tissue 3 of the mitral valve annulus to resist displacement of the annular body 10.

In some alternatives, the annular body and the anchors and paddles of various embodiments of the apparatus described herein may be made of the same material (e.g. nitinol). In these embodiments, the relative strength of the annular body 10 as compared to the anchors and/or paddles may controlled by varying the radial thickness of the components.

Figure 16:
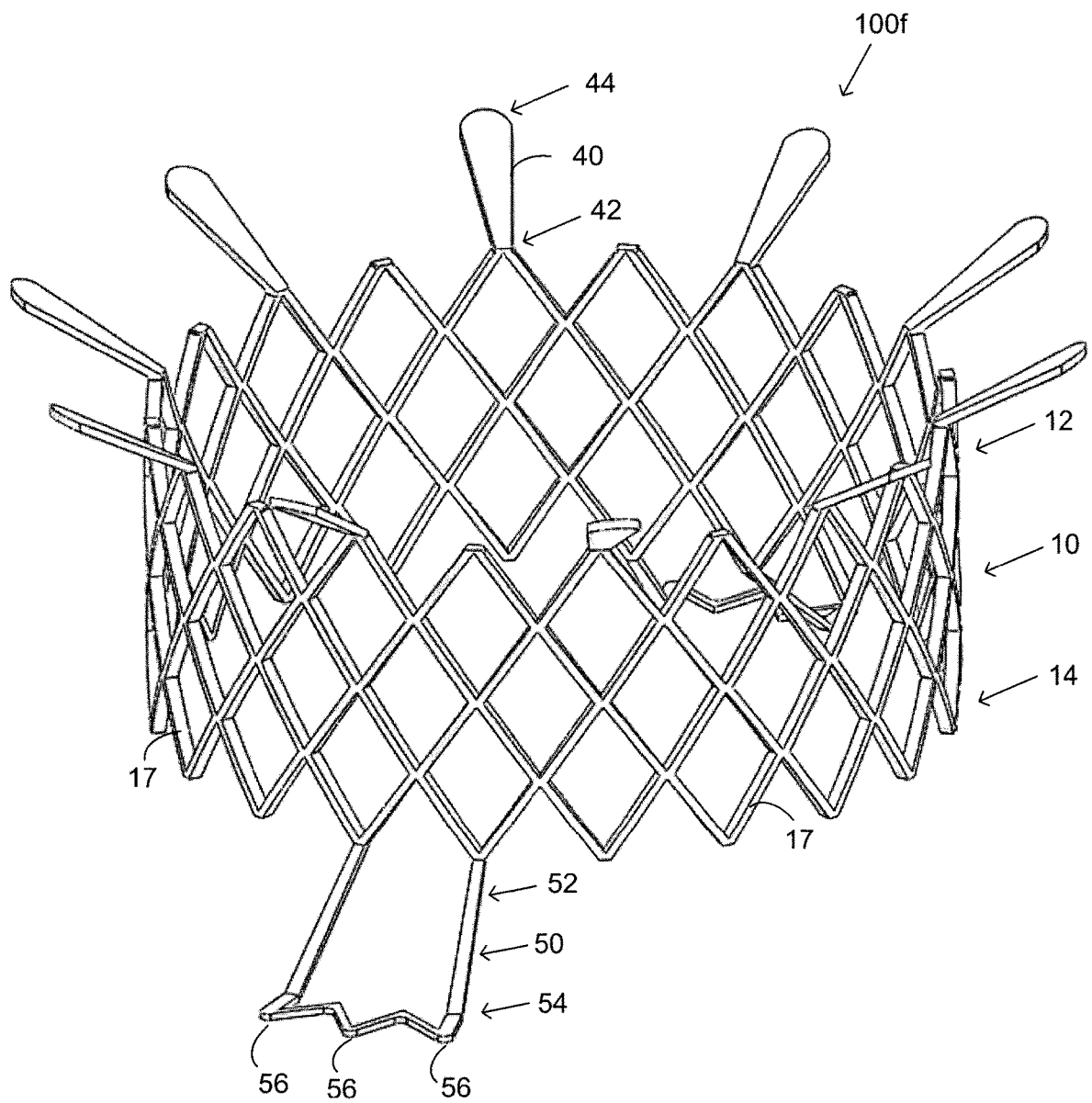
FIG. 16 is a perspective view of an apparatus for use in replacing a mitral heart valve according to another example embodiment.
Figure 17:
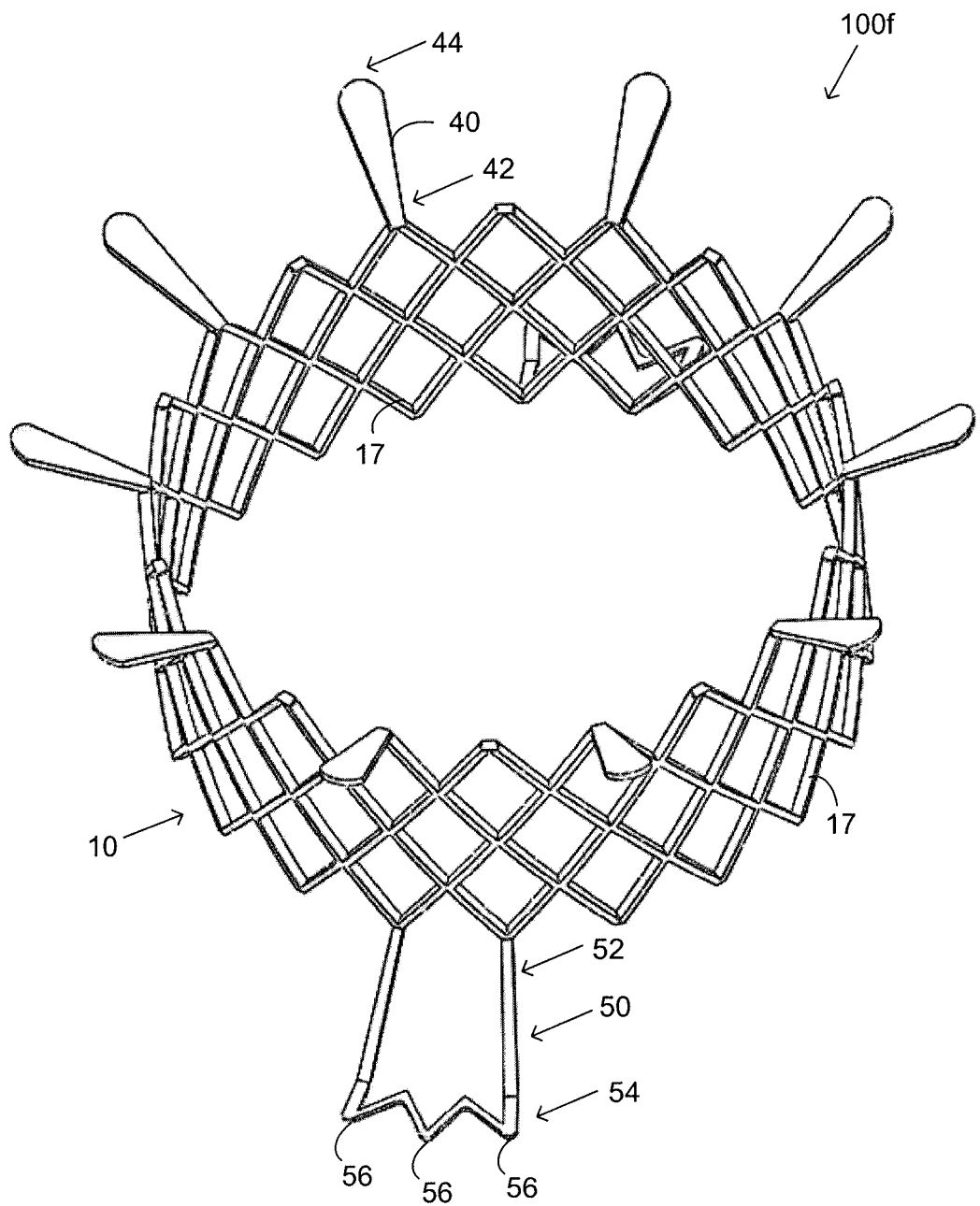
FIG. 17 is another perspective view of the apparatus of FIG. 16.
Figure 18:
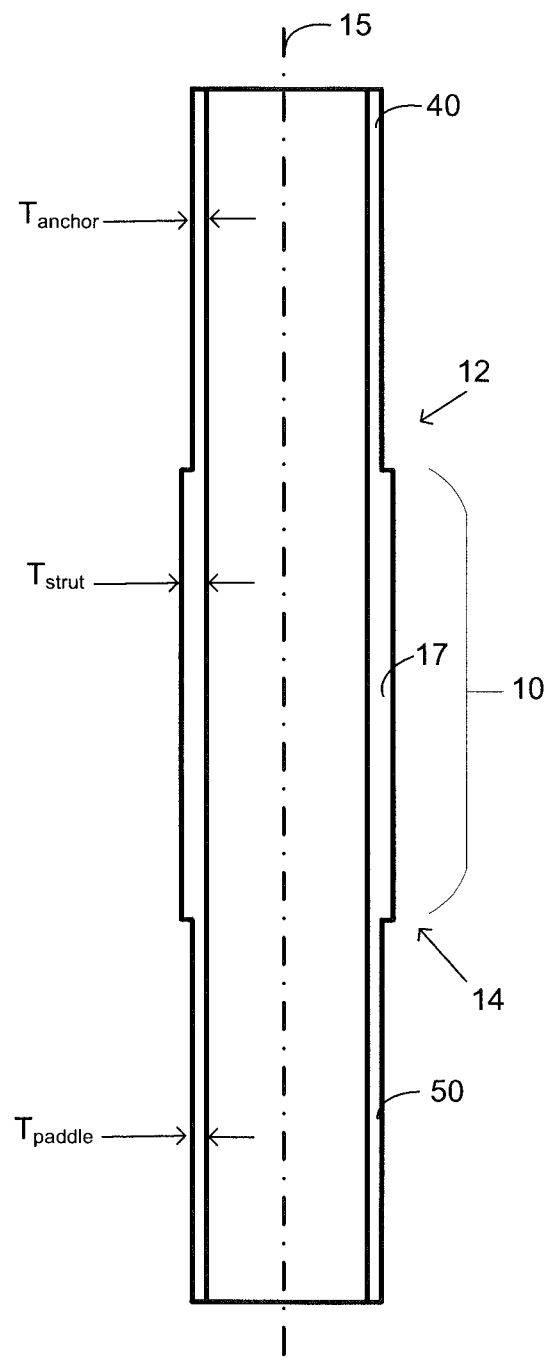
FIG. 18 is a schematic cross section view of the apparatus of FIG. 16 in a compressed state.

For example, as shown in the example apparatus 100f illustrated in FIGS. 16 and 17, the annular body 10 and the anchors 40 and paddles 50 may be made from the same material (e.g. nitinol). The annular body 10 may comprise a number of stent struts 17 having a relatively large thickness $T_{strut}$ (illustrated schematically in FIG. 18), e.g. from about 0.3 to 1.5 mm, the anchors 40 may have an anchor thickness $T_{anchor}$ that is less than the stent strut thickness, and paddles 50 may have a paddle thickness $T_{paddle}$ that is less than the stent strut thickness. In this way, while the apparatus 100f is made from the same material, main body 10 may have different mechanical properties than the thinner anchors 40 and paddles 50, due to the relatively larger stent strut thickness. As a non-limiting example, the stent strut thickness may be about 0.5 mm, the anchor thickness may be about 0.3 mm, and the paddle thickness may be about 0.3 mm.

Figure 19:
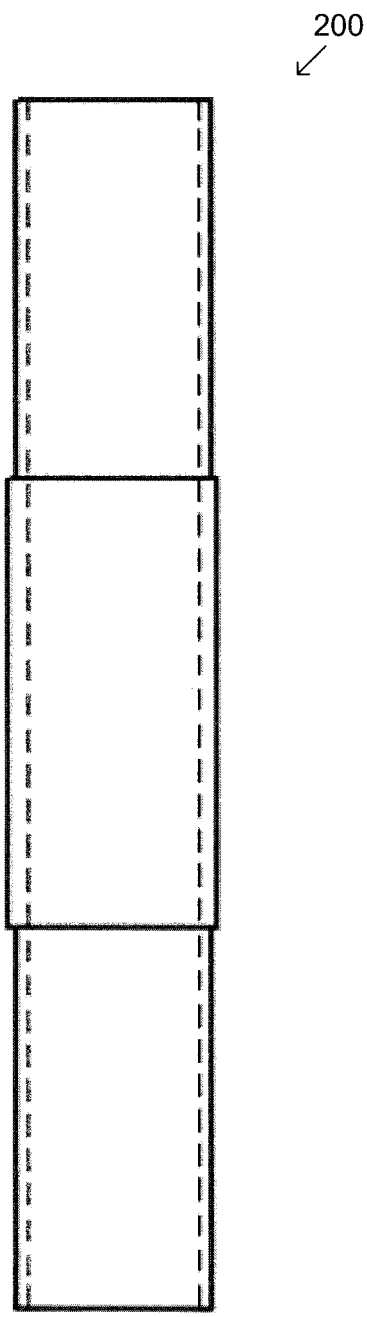
FIG. 19 is a schematic view of a tube with a variable wall thickness profile which may be laser cut to form the apparatus of FIG. 16.

An embodiment of one of the apparatus described herein in which the relative strength of the main body 10 is increased relative to the anchors 40 and/or paddles 50 by varying the radial thickness of the components may have one or more advantages. For example, when manufacturing the apparatus 100f, a nitinol tube with a variable wall thickness profile (e.g. thinner at the ends, and thicker in the middle) may be laser cut to create apparatus 100, which may reduce or eliminate the need for welding. An example of a tube 200 with a variable wall thickness is shown schematically in FIG. 19. Additionally, or alternatively, where all or substantially all of the apparatus 100f is made of a shape memory alloy (e.g. nitinol), the whole apparatus may be self-expandable, and therefore may not require balloon expansion when placing the apparatus in vivo.

Figure 7A:
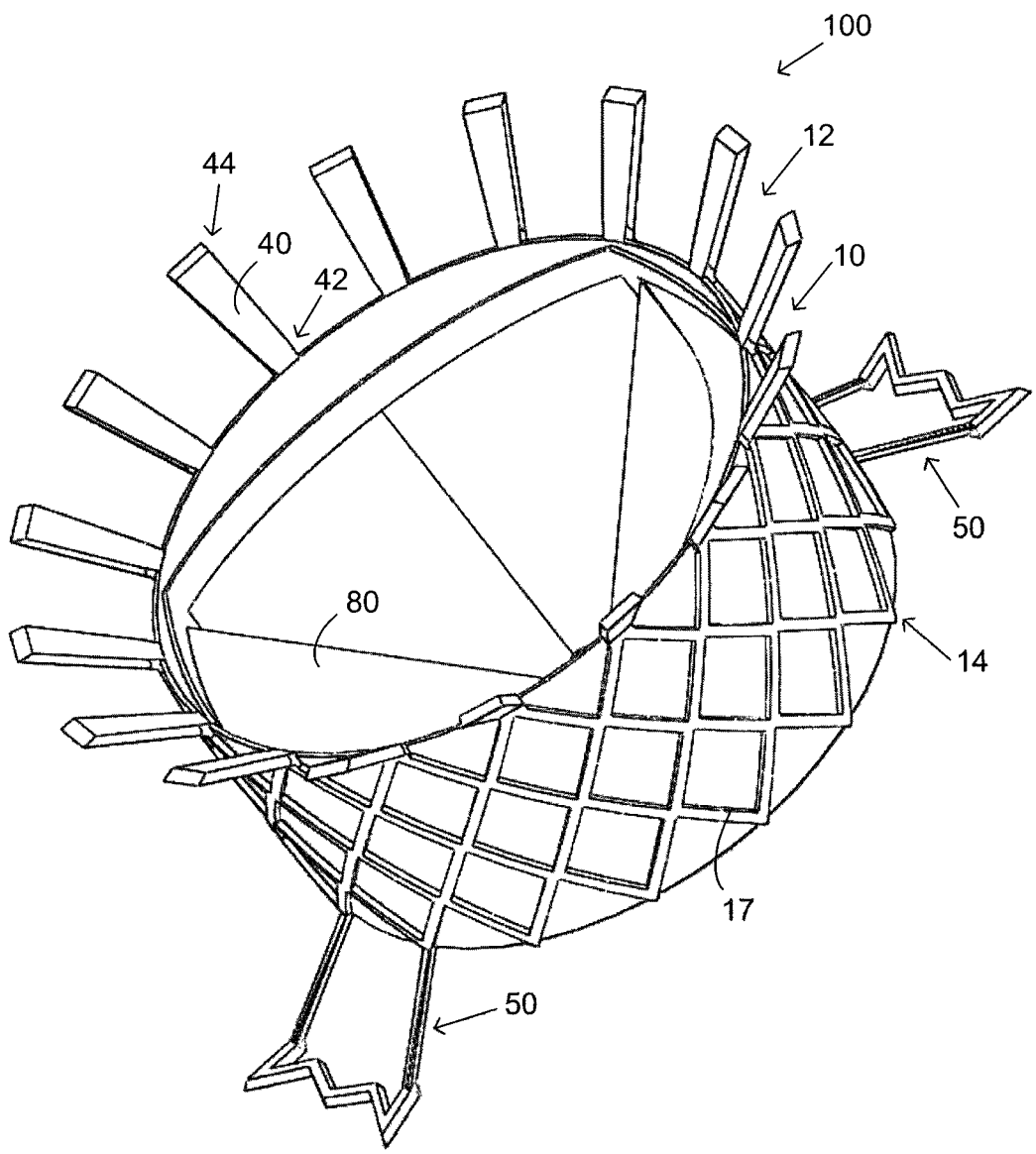
FIG. 7A is a top perspective view of the apparatus of FIG. 1 with a plurality of valve leaflets positioned in the interior volume.
Figure 7B:
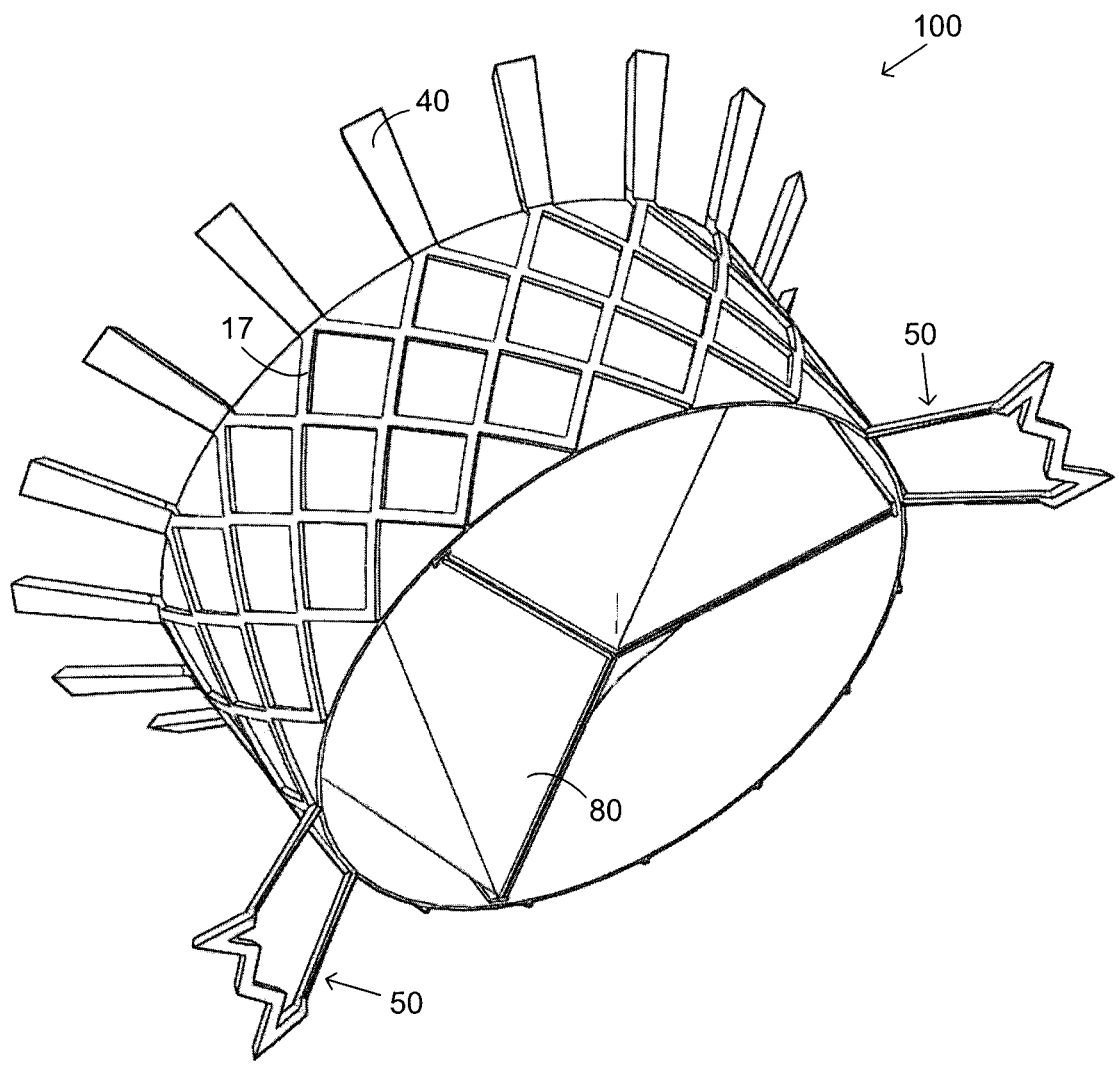
FIG. 7B is a bottom perspective view of the apparatus of FIG. 7A.
Figure 8:
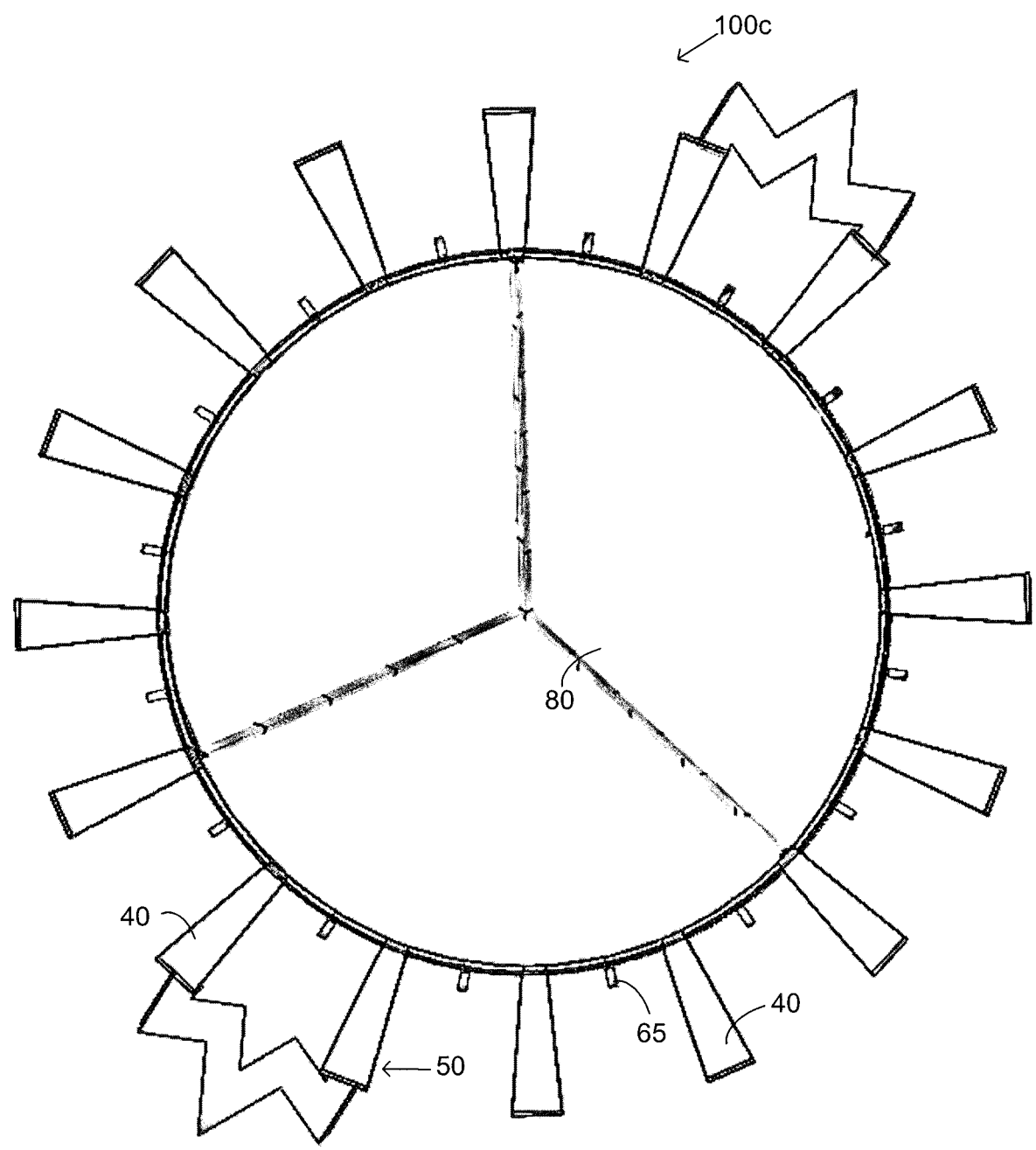
FIG. 8 is top view of the apparatus of FIG. 4 with a plurality of valve leaflets positioned in the interior volume.

As illustrated in FIGS. 7A, 7B, and 8, the apparatus may also include valve leaflets 80 positioned in the interior volume of the annular body 10. The valve leaflets 80 are configured such that, when the apparatus is in an expanded state, blood flow through the interior volume of the annular body 10 from the second end 14 towards the first end 12 is impeded, while blood flow through the interior volume of the annular body 10 from the first end 12 towards the second end 14 is permitted.

The valve leaflets 80 may be cut from natural tissue (e.g. porcine pericardium or bovine percardium) and are preferably formed before being secured to the interior of annular body 10. The leaflets 80 may be secured e.g. by sewing, or by any other suitable method. In the illustrated embodiments, three leaflets 80 are sewn into the annular body 10, although in alternative embodiments two, four, five, or more leaflets may be used.

Figure 6:
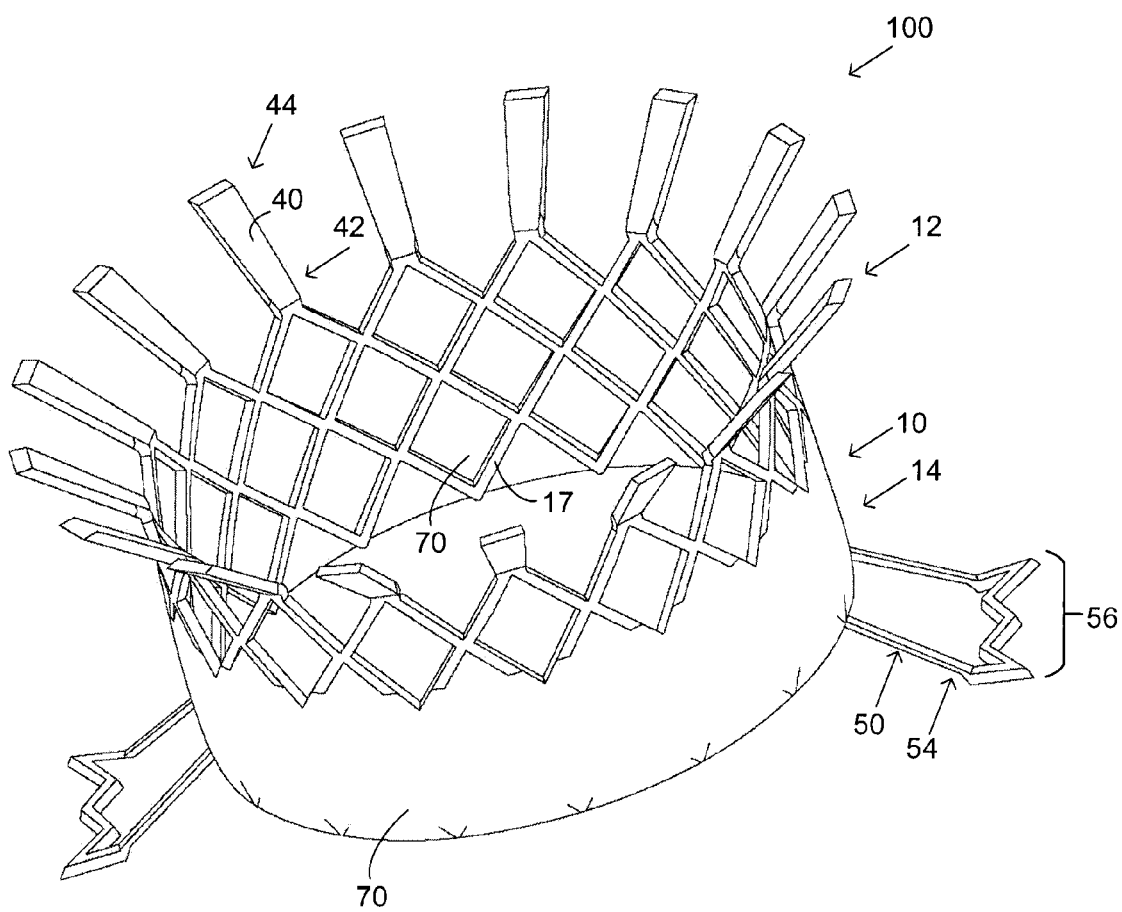
FIG. 6 is a perspective view of the apparatus of FIG. 1 with a fabric material positioned on an outer surface of the annular body.

As illustrated in FIG. 6, in another embodiment, the apparatus may also include a fabric material 70, such as Dacron, positioned on an outer surface of the annular body 10 to provide sealing between the apparatus and the surrounding tissue, e.g. to prevent blood flow from bypassing the apparatus. The fabric material 70 may be provided in a unitary sleeve, or as one or more strips of material.

Figure 11C:
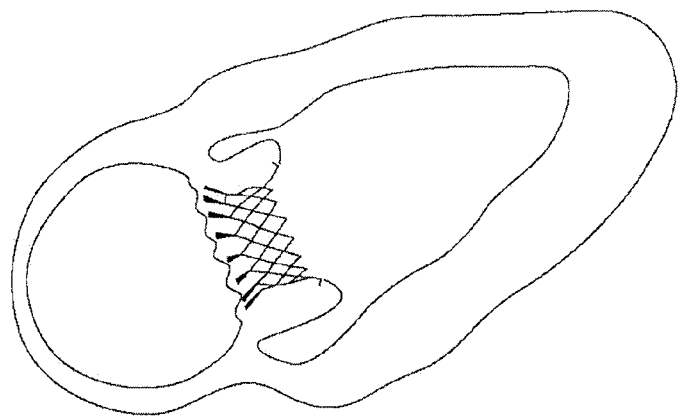
FIGS. 11A-11C illustrate a partial section view of the apparatus of FIG. 1 being positioned in a mitral annulus via the inferior vena cava and the right and left atria.
Figure 11B:
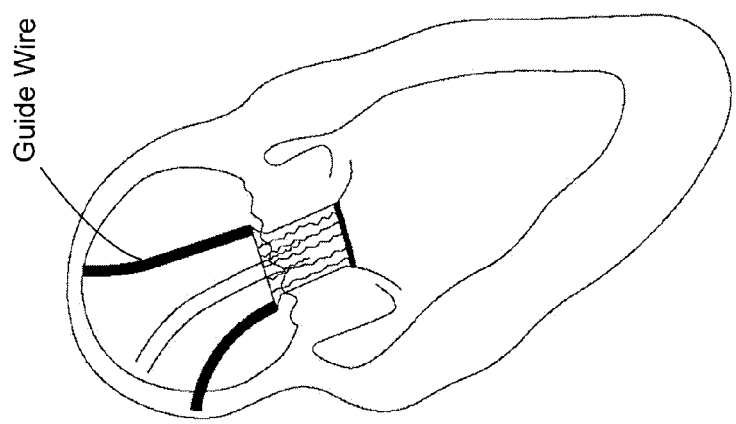
Figure 11A:
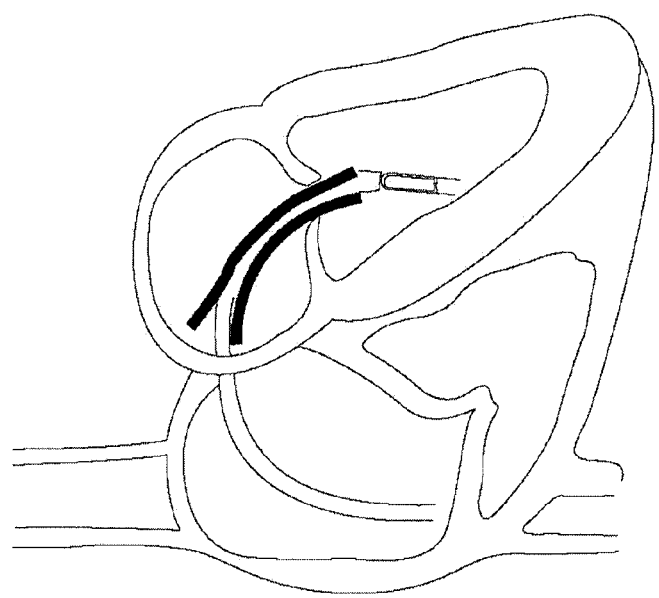
Figure 12A:
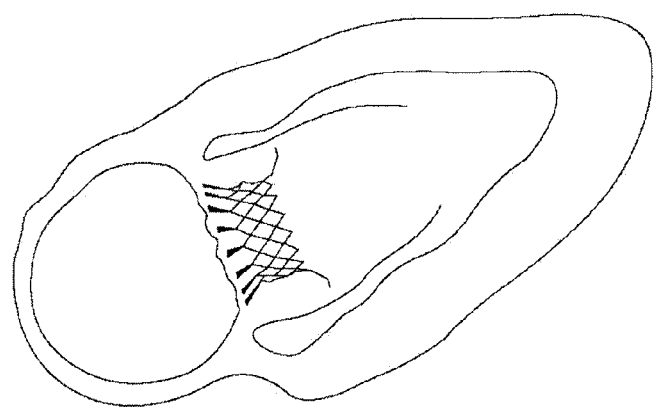
FIGS. 12A-12C illustrate a partial section view of the apparatus of FIG. 1 being positioned in a mitral annulus via direct cardiac puncture from the apex.
Figure 12B:
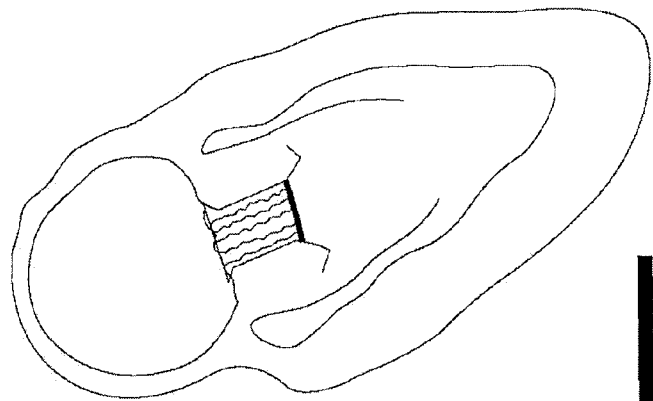
Figure 12C:
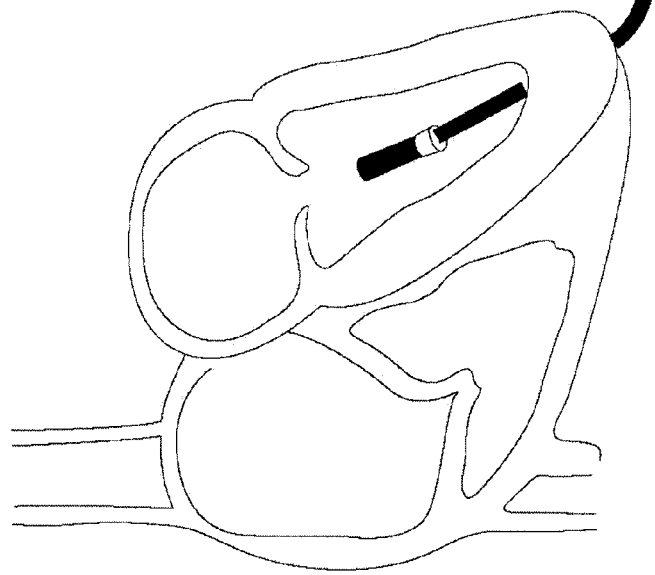
Figure 13C:
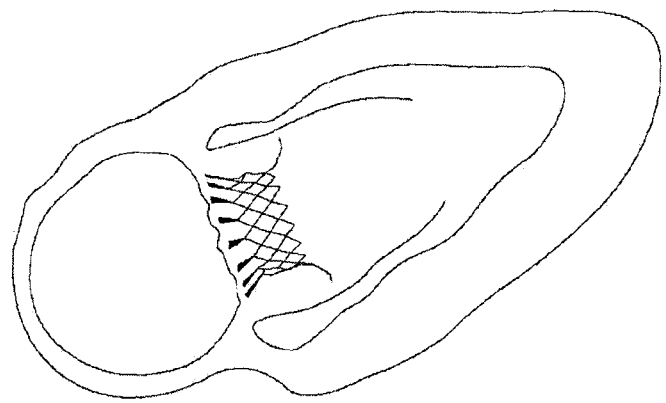
FIGS. 13A-13C illustrate a partial section view of the apparatus of FIG. 1 being positioned in a mitral annulus via direct left atrial access during open heart surgery.
Figure 13B:
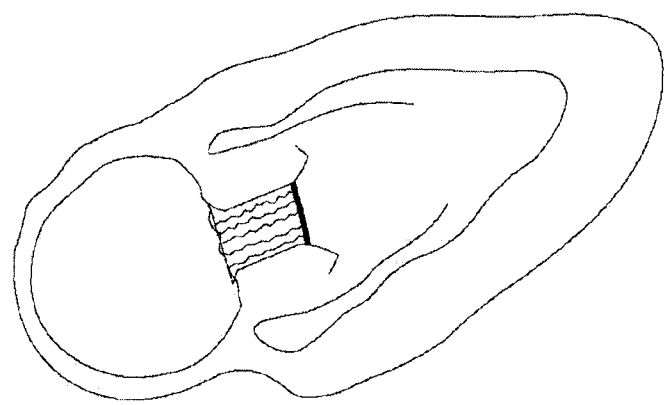
Figure 13A:
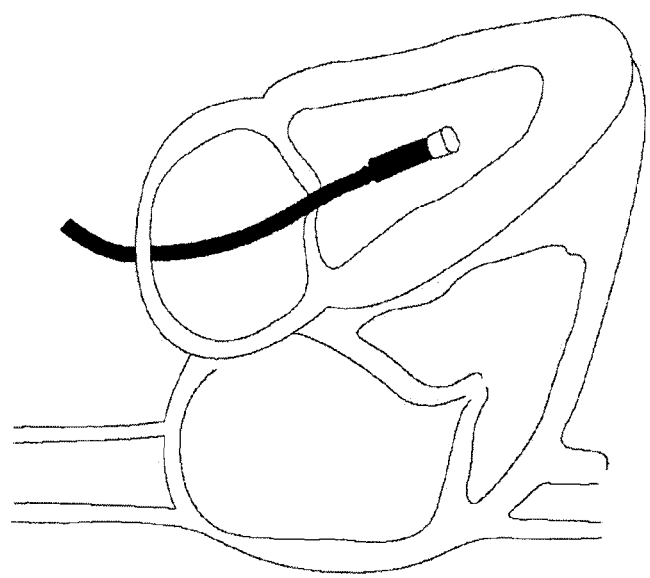

With reference to FIG. 5 and FIGS. 11A to 13C, to position one of the valve apparatuses described in accordance with the teachings herein, such as apparatus 100c, in the mitral annulus, the apparatus may be positioned on the end of a balloon catheter with the apparatus in a compressed state. The catheter may then be introduced into the heart, for example after gaining access to a vessel (artery or vein) and then being advanced to the target location (e.g. through the right femoral vein, the inferior vena cava, and then the right atrium, as illustrated in FIGS. 11A-11C) to position the apparatus in the mitral annulus. Alternatively, the apparatus may be advanced to the target location via a direct puncture of the heart, e.g. a direct cardiac puncture from the apex, as illustrated in FIGS. 12A-12C, Alternatively, the apparatus may be advanced to the target location via direct left atrial access during open heart surgery, as illustrated in FIGS. 13A-13C. After positioning the apparatus in the mitral annulus, the catheter balloon may be inflated to expand the main annular body 10. Once placed in the mitral annulus and expanded to a deployed position, the anchors 40 and the paddles 50 (and the hooks 60, where provided depending on the embodiment) of the apparatus will return to the expanded state due to their shape memory characteristics to assist in anchoring the apparatus in place.

Alternatively, in embodiments where the main annular body 10 is made of a shape memory alloy, such as apparatus 100f, a catheter may be used instead of a balloon catheter to position the apparatus, and the main annular body 10 may expand to a deployed position on its own due to its shape memory characteristics, and the anchors 40 and the paddles 50 (and the hooks 60, where provided depending on the embodiment) may return to their expanded state due to their shape memory characteristics to assist in anchoring the apparatus in place.

Figure 10:
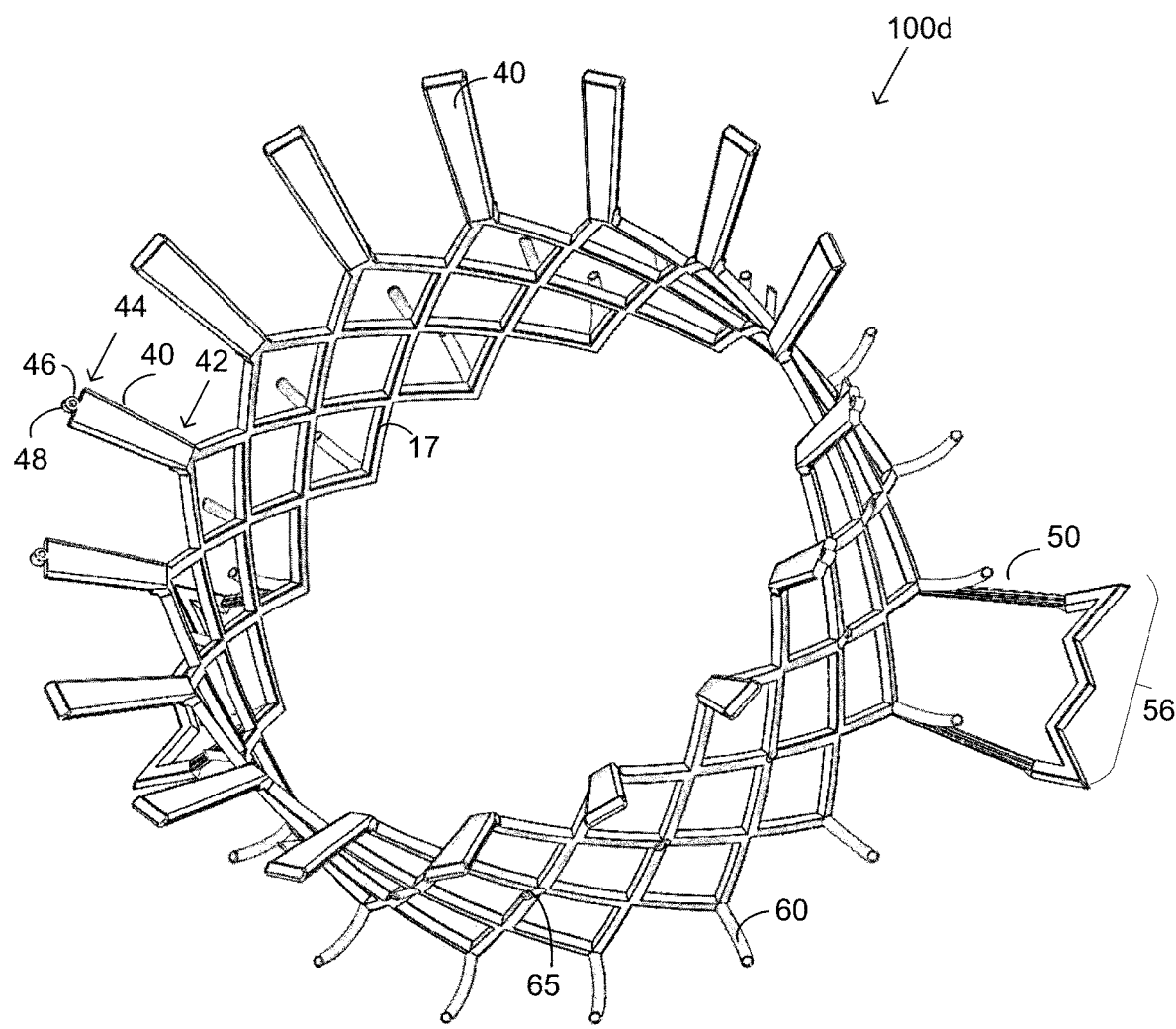
FIG. 10 is a top perspective view of an apparatus for use in replacing a mitral heart valve according to another example embodiment.

Optionally, as illustrated in FIG. 10, in an alternative embodiment, apparatus 100d may also include one or more guide projections 48 to facilitate placement of the apparatus 100d in a desired orientation. In the illustrated example, the guide projections 48 are provided at proximate distal ends 44 of the two anchor members 40, and each include a bore 46 for engaging at least one guide wire.

Alternatively, when implanting an apparatus that includes a primary annular body 20 and a secondary annular body 30 (e.g. apparatus 100b illustrated in FIG. 2), the primary annular body 20 (e.g. a Co—Cr or nitinol body 20) may be positioned and expanded in the target location (e.g. a mitral annulus) first, and the secondary annular body 30 (and attached anchors 40, paddles 50, etc.) may be subsequently positioned and expanded interior of the primary annular body 20. Such a method of implantation may obviate the need for welding and/or suturing the two annular bodies 20, 30 together before deployment. Also, implanting and expanding the annular bodies separately may facilitate implantation via vascular access, minimally invasive direct cardiac puncture, and/or during open cardiac surgery with direct visualization.

Simulation and Experimentation

The following simulation and experimental results are provided to provide examples of the performance of the apparatus as disclosed herein and/or components thereof. Unless otherwise noted, simulation results were based on embodiments in which the annular body is made of a first material (e.g. 316L stainless steel or Co—Cr), and the anchors and paddles are made of a NiTi alloy and attached to the annular body by welding.

FEA to Model Expansion of the Annular Body Using a Balloon

Ansys 16 software was used to simulate the application of load as an internal pressure applied radially within the annular body of the apparatus, to model the pressure applied by a balloon catheter to the annular body to expand the apparatus during implantation, e.g. in the mitral annulus.

The results of the analysis are summarized in Table 2. In the first set of analysis, the internal pressure due the inflation of a balloon was applied as an opening pressure of 0.1817 MPa (M Young, A Erdemir, S Stucke, R Klatte, B Davis, and J L Navia, Simulation Based Design and Evaluation of a Transcatheter Mitral Heart Valve Frame, Med Device. 2012 September; 6(3): 031005-031012. doi:10.1115/1.4007182).

For 316 L stainless steel, the maximum deformation due to this loading was about 0.093 mm. This degree of deformation is thought to be small enough not to affect any working condition of the apparatus once expanded in a mitral annulus. Also, the maximum equivalent stress produced in this material of the stent was ~341 MPa. As the yield strength of the 316 L stainless steel is about 330 MPa, this analysis indicates that the maximum stress induced by balloon expansion with a balloon pressure of 0.1817 MPa is above the yield strength of the material, thereby causing the material to undergo plastic deformation without going through the maximum strength (i.e. without rupturing or otherwise failing) and remain in an expanded form once the balloon is deflated during deployment.

TABLE 2

| Material | Balloon pressure (MPa) | Total deformation (mm) | Equivalent Elastic Strain (m/m) | Equivalent Stress (MPa) |
| --- | --- | --- | --- | --- |
| 316L Stainless Steel | 0.1817 | 0.093324 | 0.0017278 | 341.63 |
| Co—Cr | 0.1817 | 0.085372 | 0.0016163 | 319.51 |
| Co—Cr | 0.365 | 0.1715 | 0.0032469 | 641.83 |

For the Co—Cr stent, with a balloon pressure of 0.1817 MPa the maximum deformation due to this loading was about 0.085 mm. This degree of deformation is thought to be small enough not to affect any working condition of the apparatus once expanded in a mitral annulus. Also, the maximum equivalent stress produced in this material of the stent was ~319.5 MPa. As the yield strength of Co—Cr is between about 448 to 648 MPa, this analysis indicates that the maximum stress induced by balloon expansion with a balloon pressure of 0.1817 MPa is less than the yield strength of the material. Accordingly, the material will not undergo plastic deformation and will instead remain in a compressed form during deployment.

In order to determine the pressure that is sufficient and can be applied by a balloon to induce a stress above the yield point of Co—Cr, a distributed internal pressure of 0.365 MPa (3.5 atm) was applied diagonally to the stent. This is an estimate of the maximum pressure which a balloon catheter will apply in actual use, based on e.g. maximum rated burst pressures of known balloon catheters (see e.g. Edwards Lifesciences: Edwards Sapien 3, Transcatheter Heart Valve With the Edwards Commander Delivery System: http://www.accessdata.fda.gov/cdrh_docs/pdf14/P140031c.pdf, which specifies a maximum rated burst pressure (BRP) of 7 atm for the Edwards Commander Delivery System).

For the Co—Cr stent, with a balloon pressure of 0.365 MPa, the maximum deformation due to this loading was about 0.17 mm. This degree of deformation is thought to be small enough not to affect any working condition of the apparatus once expanded in a mitral annulus. Also, the maximum equivalent stress produced in the stent was ~641 MPa. As the yield strength of Co—Cr is between about 448 to 648 MPa, this analysis indicates that the maximum stress induced by balloon expansion with a balloon pressure of 0.365 MPa will be above the yield strength of the material, thereby causing the material to undergo plastic deformation without going through the maximum strength (i.e. without rupturing or otherwise failing) and remain in an expanded form once the balloon is deflated.

FEA to Model In-Situ Radial Strength

Ansys 16 software was also used to simulate the application of distributed external pressures from a lowest pressure value to a highest pressure value applied diagonally to the main annular body to determine to what degree the annular body will be affected by expected external forces once the apparatus has been deployed in the mitral valve, and to determine the expected deformation and the produced stress within the material. Simulations were first run using a pressure value of 100 Pa, to model the pressure expected to be applied to the apparatus by a mitral annulus. Subsequent analysis was performed using a pressure value of 1 atm (~101 KPa). The results are shown in Table 3.

TABLE 3

| Material | Applied pressure (KPa) | Total deformation (mm) | Equivalent Elastic Strain (mm) | Equivalent Stress (MPa) |
| --- | --- | --- | --- | --- |
| 316L Stainless Steel | 0.1 | 0.000076442 | — | 0.27036 |
| Co—Cr | 0.1 | 0.000072839 | — | 0.26089 |
| Nitinol (0.5 mm strut thickness) | 0.1 | 0.00019712 | — | 0.283 |
| Co—Cr main annular body and Nitinol secondary annular body | 0.1 | 0.00062267 | — | 0.23272 |
| 316L Stainless Steel | 101.325 | 0.076411 | 0.0013586 | 268.73 |
| Co—Cr | 101.325 | 0.072809 | 0.0013111 | 259.32 |
| Nitinol (0.5 mm strut thickness) | 101.325 | 0.19973 | 0.0037115 | 285.93 |
| Co—Cr main annular body and Nitinol secondary annular body | 101.325 | 0.063092 | 0.0021816 | 235.81 |

For a stainless steel annular body, when an external radial pressure of 100 Pa was applied, the calculated deformation was negligible, and the calculated stress of 0.27 MPa was quite low considering the yield stress of ~331 MPa for stainless steel.

For a Co—Cr annular body, when an external radial pressure of 100 Pa was applied, the calculated deformation was also negligible, and the calculated stress of 0.26 MPa was quite low considering the yield stress of ~448-648 MPa for Co—Cr alloys.

For a nitinol stent with a strut thickness of 0.5 mm for the main body 10, when an external radial pressure of 100 Pa was applied, the calculated deformation was negligible, and the calculated stress of 0.283 was quite low considering the yield stress of 195-690 MPa for Austenite Nitinol (as shown in Table 1).

For a stent with a Co—Cr primary annular body and a nitinol secondary annular body (e.g. apparatus 100b illustrated in FIG. 2), when an external radial pressure of 100 Pa was applied, the calculated deformation was negligible, and the calculated stress of 0.233 was quite low considering the yield stresses of ~448-648 MPa for Co—Cr (as shown in Table 1) and 195-690 MPa for Austenite Nitinol.

To model a 'worst case' pressure expected to be applied by the mitral annulus on the mitral valve apparatus following implantation, a pressure of 1 atm (~101 kPa) was used to simulate the resulting stress, strain, and deformation of the main annular body of the mitral valve apparatus, although this amount of pressure is thought to be unrealistically high considering the amount of pressure exerted by the mitral annulus during the normal operation of a typical human heart (e.g. ~100 Pa).

For a stainless steel annular body and a pressure of 1 atm, the calculated deformation was negligible, and the calculated stress of ~268 MPa was below the yield stress of ~331 MPa for stainless steel.

For a Co—Cr annular body and a pressure of 1 atm, the calculated deformation was negligible, and the calculated stress of ~259 MPa was below the yield stress of ~448-648 MPa for Co—Cr.

For a nitinol stent with a strut thickness of 0.5 mm for the main body 10, when an external radial pressure of 1 atm was considered, the calculated deformation was negligible and the calculated stress of 285.93 MPa was within the lower range of the yield stress of 195-690 MPa for Austenite Nitinol.

For a stent with a Co—Cr primary annular body and a nitinol secondary annular body, when an external radial pressure of 1 atm was considered, the calculated deformation was negligible, and the calculated stress of 235.8 was below the yield stresses of ~448-648 MPa for Co—Cr and within the lower range of the yield stress of 195-690 MPa for Austenite Nitinol.

Ansys 16 software was also used to simulate the application of distributed external pressures on a stainless steel annular body using pressure values of 150 mmHg (~20 kPa) and 50 mmHg (~6.7 kPa), to model the pressure expected to be applied during systolic and diastolic phases, respectively, of the cardiac cycle. The results are shown in Table 4.

TABLE 4

| Material | Applied pressure (KPa) | Total deformation (mm) | Equivalent Elastic Strain (m/m) | Equivalent Stress (MPa) |
|---|---|---|---|---|
| 316L Stainless Steel | 20 | 0.014567 | 0.00026378 | 52.174 |
| Co—Cr | 20 | 0.015332 | 0.00012975 | 25.393 |
| Nitinol (0.5 mm strut thickness) | 20 | 0.038175 | 0.00070848 | 54.581 |
| Co—Cr main annular body and Nitinol secondary annular body | 20 | 0.024068 | 0.00026404 | 36.608 |
| 316L Stainless Steel | 6.67 | 0.0048555 | 0.000087927 | 17.391 |
| Co—Cr | 6.67 | 0.0051361 | 0.000043467 | 8.507 |
| Nitinol (0.5 mm strut thickness) | 6.67 | 0.012789 | 0.00023734 | 18.2 |
| Co—Cr main annular body and Nitinol secondary annular body | 6.67 | 0.0082003 | 0.000088545 | 12.258 |

For a stainless steel annular body and a pressure of 20 Pa, the calculated deformation was negligible, and the calculated stress of ~52 MPa was quite low considering the yield stress of ~331 MPa for stainless steel. For a pressure of 6.67 Pa, the calculated deformation was again negligible, and the calculated stress of ~17 MPa was also well below the yield stress of ~331 MPa for stainless steel.

For a Co—Cr annular body and a pressure of 20 Pa, the calculated deformation was negligible, and the calculated stress of ~25 MPa was quite low considering the yield stress of ~448-648 MPa for Co—Cr. For a pressure of 6.67 Pa, the calculated deformation was again negligible, and the calculated stress of ~8.5 MPa was also well below the yield stress of ~448-648 MPa for Co—Cr.

For a nitinol annular body and a pressure of 20 Pa, the calculated deformation was negligible, and the calculated stress of ~54 MPa was quite low considering the yield stress of ~195-690 MPa for nitinol. For a pressure of 6.67 Pa, the calculated deformation was again negligible, and the calculated stress of ~18 MPa was also well below the yield stress of ~195-690 MPa for nitinol.

For a stent with a Co—Cr primary annular body and a nitinol secondary annular body and a pressure of 20 Pa, the calculated deformation was negligible, and the calculated stress of ~36 MPa was quite low considering the yield stresses of ~448-648 MPa for Co—Cr and ~195-690 MPa for nitinol. For a pressure of 6.67 Pa, the calculated deformation was again negligible, and the calculated stress of ~12 MPa was also well below the yield stress of ~448-648 MPa for Co—Cr and ~195-690 MPa for nitinol.

Fluid Flow Analysis to Model Blood Flow Through the Apparatus In-Situ

Solidworks software (Release 2015) was used to simulate the resultant shear stress due to blood flowing through the annular body and the valve leaflets. The results are shown in Table 5.

TABLE 5

| Parameter | Minimum | Maximum |
|---|---|---|
| Pressure [Pa] | −16889.06 | 15728.42 |
| Density (Fluid) [kg/m^3] | 1003.00 | 1003.00 |
| Velocity [m/s] | 0 | 1.905 |
| Velocity (X) [m/s] | −0.328 | 0.266 |
| Velocity (Y) [m/s] | 0 | 1.905 |

TABLE 5-continued

| Parameter | Minimum | Maximum |
|---|---|---|
| Velocity (Z) [m/s] | −0.260 | 0.352 |
| Vorticity [1/s] | 0.15 | 1149.78 |
| Velocity RRF [m/s] | 0 | 1.905 |
| Velocity RRF (X) [m/s] | −0.328 | 0.266 |
| Velocity RRF (Y) [m/s] | 0 | 1.905 |
| Velocity RRF (Z) [m/s] | −0.260 | 0.352 |
| Relative Pressure [Pa] | −118214.06 | −85596.58 |
| Heat Transfer Coefficient [W/m^2/K] | 0 | 0 |
| Surface Heat Flux [W/m^2] | 0 | 0 |

According to the simulated model, the minimum shear stress induced on the valve apparatus as a result of the blood flow through the valve was 0.02 Pa, and the maximum value of shear stress according to the model was 40.54 Pa. In view of the yield strength and strength of stainless steel and cobalt chromium alloys (e.g. somewhere between 300-600 MPa), the induced shear stress is expected to be negligible, therefore the blood flow does not appear to be a major factor that has to be taken into account when considering the design strength of the stent apparatus.

Fatigue Analysis

Fatigue analysis has been performed using Ansys FEA Software. Table 5 is a summary from the results of this analysis.

TABLE 6

| Material | Life (Cycles) | SAFETY FACTOR |
|---|---|---|
| Stainless steel | 1e6 | >3 |
| Co—Cr | 1e9 | >8 |
| Nitinol (0.5 mm strut thickness) | 1e10 | >14 |
| Co—Cr main annular body and Nitinol secondary annular body | 1e9 | >15 |

As shown in Table 5, the nitinol annular body and the Co—Cr, nitinol combination have the highest safety factors.

Weld Strength Analysis

To test the welding of nitinol to a Co—Cr alloy, a sample of nitinol was laser welded to a sample of Co—Cr. The strength of the weld was then tested by applying a force to the weld joint and measuring the strength of the joint using a force sensor.

Figure 15:
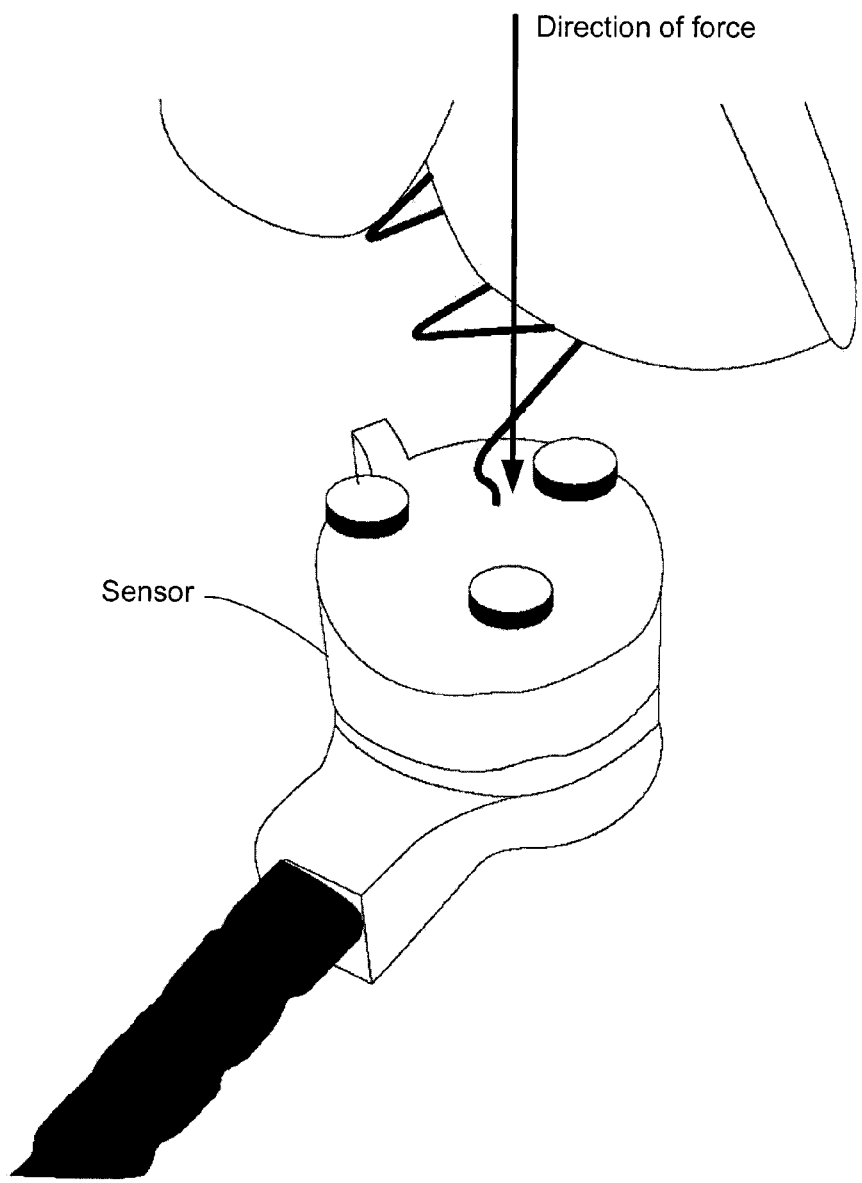
FIG. 15 shows experimental equipment used to test the strength of a nitinol to Co—Cr weld.

As shown in FIG. 15, a force sensor (ATI F/T sensor system from ATI Industrial Automation) connected to a computer via a data acquisition card was used to measure the force applied by pressing the welded components towards the force sensor. Specifically, pressure was applied to the force plate of the sensor by pointing the welded parts towards the plate in a Z-direction as illustrated in FIG. 15. During the application of force, the data acquisition card connected to the computer recorded the force applied to the sensor. As a result of this experiment, it was determined that a force up to about 2 Newtons can be applied to the weld without any defect or collapse in the joint contact. Based on a 'worst case' applied pressure of 1 atm as noted above, which is equivalent to 101325 N/m$^2$ (about 10$^5$ N/m$^2$), and an approximate outer surface area of 0.4 mm×0.4 mm (i.e. 0.16×10$^{-6}$ m$^2$) of the valve apparatus surface area upon which this pressure is applied, then the 'worst case' force that can be applied to such a surface area is about 0.016 N, which is less than the maximum experimental force of 2 Newtons.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the teachings herein as defined in the claims appended hereto. The scope of the claims should not be limited by the preferred embodiments and examples, but should be given the broadest interpretation consistent with the description as a whole.

The invention claimed is:

1. An apparatus for placement in a mitral valve of a heart, the apparatus comprising:
   an annular body made from a first material and having first and second spaced apart ends, a longitudinally extending axis, and an interior volume extending from the first end to the second end;
   a plurality of first anchor members made from a second material and extending from the first end of the annular body; and
   at least two paddles made from the second material and extending downstream from the second end of the annular body, each of the at least two paddles having at least two prongs extending away from and along a longitudinal axis of a distal end of the at least two paddles and the at least two prongs are configured to contact and engage chordae tendineae of the heart;
   wherein, in a compressed state, the annular body has a first diameter, the plurality of first anchor members extend substantially longitudinally from the first end of the annular body, and the at least two paddles extend substantially longitudinally from the second end of the annular body, and
   wherein, in an expanded state, the annular body has a second diameter larger than the first diameter, the plurality of first anchor members extend longitudinally and radially outward from the first end of the annular body for engaging an upstream portion of a mitral valve annulus to resist displacement of the annular body towards a left ventricle, and the at least two paddles extend longitudinally downstream from the second end of the annular body and radially outward from the second end of the annular body for directly contacting and engaging the chordae tendineae of the heart.

2. The apparatus of claim 1, further comprising a plurality of second anchor members made from the second material and extending from the second end of the annular body, wherein, in the compressed state, the plurality of second anchor members extend substantially longitudinally from the second end of the annular body, and wherein, in the expanded state, the plurality of second anchor members extend longitudinally and radially outward from the second end of the annular body for engaging a subvalvular apparatus to resist displacement of the annular body towards a left atrium.

3. The apparatus of claim 2, wherein an average length of the plurality of first anchor members is larger than an average length of the plurality of second anchor members.

4. The apparatus of claim 3, wherein at least some of the plurality of second anchor members are hook-shaped.

5. The apparatus of claim 1, wherein the plurality of first anchor members are welded to the annular body, and wherein the at least two paddles are welded to the annular body.

6. The apparatus of claim 1, wherein the annular body comprises a plurality of diamond shaped openings.

7. The apparatus of claim 1, further comprising at least two guide projections for engaging at least one guide wire for facilitating placement of the apparatus within the mitral valve annulus.

8. The apparatus of claim 7, wherein the guide projections are provided on the plurality of first anchor members.

9. The apparatus of claim 1, wherein the annular body comprises a first portion made from the first material and a second portion made from the second material, wherein the plurality of first anchor members extend from a first end of the second portion, and wherein the at least two paddles extend from a second end of the second portion.

10. The apparatus of claim 9, wherein the second portion, the plurality of first anchor members, and the at least two paddles are integrally formed.

11. The apparatus of claim 9, wherein the first portion is secured to the second portion by at least one weld.

12. The apparatus of claim 1, further comprising a fabric material positioned on at least a portion of an outer surface of the annular body.

13. The apparatus of claim 12, wherein the fabric material comprises a Dacron fabric.

14. The apparatus of claim 1, further comprising at least two valve leaflets positioned in the interior volume and configured such that, in the expanded state, blood flow through the interior volume towards the first end is impeded.

15. The apparatus of claim 1, wherein the annular body is configured to be expanded from the compressed state to the expanded state using a balloon catheter.

16. The apparatus of claim 1, wherein the first material is a cobalt chromium alloy and the second material is shape-memory alloy.

17. The apparatus of claim 16, wherein the second material is a nitinol alloy.

18. The apparatus of claim 1, wherein the first material is a shape memory alloy, and the second material is the same shape-memory alloy as the first material.

19. The apparatus of claim 18, wherein the first material is a nitinol alloy.

20. The apparatus of claim 1, wherein the annular body, the plurality of deployable first anchor members, and the at least two paddles are made from the same material.

21. The apparatus of claim 1, wherein the first material and the second material are a shape-memory alloy.

22. The apparatus of claim 21, wherein the shape-memory alloy is a nitinol alloy.

23. The apparatus of claim 1, wherein the at least two paddles and the plurality of first anchor members are deployable.

24. The apparatus of claim 1, wherein:
the annular body comprises one or more stent struts having a stent strut thickness;
the plurality of first anchor members have an anchor member thickness in a radial direction that is less than the stent strut thickness; and
the at least two paddles have a paddle thickness in the radial direction that is less than the stent strut thickness.

25. The apparatus of claim 24, wherein the anchor member thickness and the paddle thickness are substantially the same.

26. The apparatus of claim 24, wherein the stent strut thickness is about 0.5 mm and the anchor member thickness is about 0.3 mm.

27. An apparatus for placement in a mitral valve of a heart, the apparatus comprising:
an annular body made from a first material and having first and second spaced apart ends, a longitudinally extending axis, and an interior volume extending from the first end to the second end;
a plurality of anchor members made from a second material and extending from the first end of the annular body; and
at least two paddles made from the second material and extending from the second end of the annular body, each of the at least two paddles having at least two arms joined by at least two prongs at a distal end thereof defining a sawtooth pattern and the at least two prongs are configured to contact and engage chordae tendineae of the heart;
wherein the first material has a higher radial strength than the second material,
wherein, in a compressed state, the annular body has a first diameter, the plurality of anchor members extend substantially longitudinally from the first end of the annular body, and the at least two paddles extend substantially longitudinally from the second end of the annular body,
wherein, in an expanded state, the annular body has a second diameter larger than the first diameter, the plurality of anchor members extend longitudinally and radially outward from the first end of the annular body for engaging an upstream portion of a mitral valve annulus to resist displacement of the annular body towards a left ventricle, and the at least two paddles extend longitudinally and radially outward from the second end of the annular body for contacting and engaging the chordae tendineae of the heart.

* * * * *